United States Patent
Homan et al.

(10) Patent No.: US 10,532,105 B2
(45) Date of Patent: Jan. 14, 2020

(54) FORMULATIONS FOR IMPROVING THE EFFICACY OF HYDROPHOBIC DRUGS

(71) Applicant: Peptinovo Biopharma, LLC, Ann Arbor, MI (US)

(72) Inventors: Reynold Homan, Ann Arbor, MI (US); William L. Elliott, Ann Arbor, MI (US)

(73) Assignee: Peptinovo Biopharma, LLC., Ann Arbor, MI (US)

( * ) Notice: Subject to any disclaimer, the term of this patent is extended or adjusted under 35 U.S.C. 154(b) by 0 days.

(21) Appl. No.: 15/743,098

(22) PCT Filed: Jul. 8, 2016

(86) PCT No.: PCT/US2016/041544
§ 371 (c)(1),
(2) Date: Jan. 9, 2018

(87) PCT Pub. No.: WO2017/011312
PCT Pub. Date: Jan. 19, 2017

(65) Prior Publication Data
US 2019/0076544 A1    Mar. 14, 2019

Related U.S. Application Data

(60) Provisional application No. 62/190,909, filed on Jul. 10, 2015.

(51) Int. Cl.
| | |
|---|---|
| *A61K 47/60* | (2017.01) |
| *C07K 14/00* | (2006.01) |
| *A61P 35/00* | (2006.01) |
| *A61K 9/00* | (2006.01) |
| *A61K 9/107* | (2006.01) |
| *A61K 38/16* | (2006.01) |
| *A61K 9/127* | (2006.01) |

(52) U.S. Cl.
CPC ............ *A61K 47/60* (2017.08); *A61K 9/0019* (2013.01); *A61K 9/107* (2013.01); *A61K 9/127* (2013.01); *A61K 38/16* (2013.01); *A61P 35/00* (2018.01); *C07K 14/00* (2013.01)

(58) Field of Classification Search
CPC ........ A61K 47/60; A61K 9/107; A61K 9/127; A61K 9/0019; A61K 38/16; C07K 14/00; A61P 35/00
See application file for complete search history.

(56) References Cited

U.S. PATENT DOCUMENTS

| | | | |
|---|---|---|---|
| 6,046,166 A | 4/2000 | Dasseux et al. | |
| 6,287,590 B1 | 9/2001 | Dasseux | |
| 6,376,464 B1 | 4/2002 | Dasseux et al. | |
| 6,455,088 B1 | 9/2002 | Dasseux | |
| 7,189,411 B2 | 3/2007 | Dasseux | |
| 7,273,848 B2 | 9/2007 | Dasseux et al. | |
| 8,143,224 B2 | 3/2012 | Smith et al. | |
| 8,536,117 B2 | 9/2013 | Smith et al. | |
| 8,568,766 B2 | 10/2013 | Anantharamaiah et al. | |
| 8,603,999 B2 | 12/2013 | Drummond et al. | |
| 8,728,749 B2 | 5/2014 | Auerbach et al. | |
| 8,758,749 B2 | 6/2014 | Frendeus et al. | |
| 9,051,393 B2 | 6/2015 | Smith et al. | |
| 2003/0045460 A1 | 3/2003 | Fogelman et al. | |
| 2004/0234588 A1 | 11/2004 | Lu et al. | |
| 2004/0266662 A1 | 12/2004 | Rye et al. | |
| 2009/0110739 A1 | 4/2009 | Lacko et al. | |
| 2011/0020242 A1 | 1/2011 | Zheng et al. | |
| 2014/0024061 A1 | 1/2014 | Auerbach et al. | |
| 2016/0074473 A1 | 3/2016 | Turner et al. | |

FOREIGN PATENT DOCUMENTS

| | | |
|---|---|---|
| WO | 2003096983 A2 | 11/2003 |
| WO | 2004050062 A2 | 6/2004 |
| WO | 2005070400 A1 | 8/2005 |
| WO | 2009055538 A1 | 4/2009 |
| WO | 2009073984 A1 | 6/2009 |
| WO | 2009155366 A2 | 12/2009 |
| WO | 2016011049 A2 | 1/2016 |
| WO | 2016019333 A1 | 2/2016 |

OTHER PUBLICATIONS

Ahsan, H. et al., "Pharmacological potential of tocotrienols: a review," Nutrition & Metab, 2014, pp. 1-22, vol. 11, No. 52.
Cao, W. et al., "Synthesis and Evaluation of a Stable Bacteriochlorophyll-Analog and Its Incorporation into High-Density Lipoprotein Nanoparticles for Tumor Imaging," Bioconjug Chem,2009, pp. 2023-2031, vol. 20, No. 11.
Dong, H. et al., "Long-circulating 15 nm micelles based on amphiphilic 3-helix peptide-PEG conjugates," ACS Nano, 2012, pp. 5320-5329, vol. 6 No. 6.
Fournier, E. et al., "A Novel One-Step Drug-Loading Procedure for Water-Soluble Amphiphilic Nanocarriers," Pharma Res, 2004, pp. 962-968, vol. 21 No. 6.
Hessa, T. et al., "Recognition of transmembrane helices by the endoplasmic reticulum translocon," Nature, 2005, pp. 377-381, vol. 433.
Husain, K. et al., "Vitamin E d-Tocotrienol Augments the Antitumor Activity of Gemcitabine and Suppresses Constitutive NF-kB Activation in Pancreatic Cancer," Mol Cancer Ther, 2011, pp. 2363-2372, vol. 10, No. 12.
International Search Report and Written Opinion for PCT/US2016/041544, dated Dec. 8, 2017, 11 pgs.
Lacko A. et al, "High density lipoprotein complexes as delivery vehicles for anticancer drugs", AntiCancer Research, 2002, pp. 2045-2050, vol. 22, No. 4.

(Continued)

*Primary Examiner* — Karlheinz R. Skowronek
*Assistant Examiner* — Li N Komatsu
(74) *Attorney, Agent, or Firm* — Honigman LLP; Cynthia M. Bott; Jonathan P. O'Brien

(57) ABSTRACT

Novel amphiphilic peptide, peptide amphiphile lipid micelles, processes for making peptide amphiphile lipid micelles comprising an amphiphilic peptide and phospholipid and optionally comprising a cargo molecule, and methods of use.

21 Claims, 6 Drawing Sheets
Specification includes a Sequence Listing.

(56) References Cited

OTHER PUBLICATIONS

Ma P et al., "Paclitaxel Nano-Delivery Systems: A Comprehensive Review," J Nanomed Nanotechol, 2013, pp. 1-16, vol. 4, No. 2.

Ng, K.K. et al., "Lipoprotein-inspired nanoparticles for cancer theranostics", Acc Chem Res, 2011, pp. 1105-1113, vol. 44, No. 10.

Pownall, H.J., et al., "Helical amphipathic moment: application to plasma lipoproteins," FEBS Letters, 1983, pp. 17-23, vol. 159, No. 1, 2.

Qian F. et al., "Formation of Zinc-Peptide Spherical Microparticles During Lyophilization from tert-Butyl Alcohol/Water Co-solvent System," Pharmaceutical Research, 2008, pp. 2799-2806, vol. 25, No. 12.

Sabnis N. et al., "Drug delivery via lipoprotein-based carriers," Therapeutic Delivery, 2012, pp. 599-608, vol. 3, No. 5.

Sethi A. et al., "Asymmetry in the Lipid Affinity of Bihelical Amphipathic Peptides," J Biol Chem, 2008, pp. 32273-32282, vol. 283, No. 7.

Smith R. et al., "Dynamaics of the Intrinsic Membrane Polypeptide Grgamicidin a in phospholipid Bilayers A solid-state 13C Nuclear Magnetic Resonance study," Biophys. J., 1986, pp. 117-118, vol. 49.

Stevens P. J. et al., "A Folate Receptor-Targeted Lipid Nanoparticle Formulation for a Lipophilic Paclitaxel Prodrug," Pharmaceutical Research, 2004, pp. 2153-2157, vol. 21, No. 12.

Teagarden D. et al., "Practical aspects of lyophilization using non-aqueous co-solvent systems," European J. of Pharm Sci , 2002, pp. 115-133, vol. 15.

Wittaya-Areeku S. et al., "Freeze-Drying of tert-Butyl Alcohol/Water Cosolvent Systems: Effects of Formulation and Process Variables on Residual Solvents," Journal of Pharmaceutical Sciences, 1998, pp. 491-495, vol. 87, No. 4.

Zhang, Z.H. et al, "Biomimetic nanocarrier for direct cytosolic drug delivery", Angew Chem Int Ed, 2009, pp. 9171-9175, vol. 48.

Zheng Y. et al., "Scavenger Receptor B1 is a Potential Biomarker of Human Nasopharyngeal Carcinoma and Its Growth is Inhibited by HDL-mimetic Nanoparticles," Theranostics, 2013, pp. 477-486, vol. 3, No. 7.

Anantharamaiah, G. M. et al., "Studies of Synthetic Peptide Analogs of the Amphipathic Helix," J Biol Chem. 1985, pp. 10248-10255, vol. 260, No. 18.

Anantharamaiah, G. M. et al., "Use of Synthetic Peptide analogues to Localize Lecithin:Cholesterol Acyltransferase Activating Domain in Apolipoprotein A-I," Arteriosclerosis, 1990, pp. 95-105, vol. 10, No. 1.

Cormode, D. P. et al., "Comparison of Synthetic High Density Lipoprotein (HDL) Contrast Agents for MR Imaging of Atherosclerosis," Bioconjugate Chem., 2009, pp. 937-943, vol. 20, No. 5.

Datta, G. et al., "Effects of Increasing Hydrophobicity on the Physical-Chemical and Biological Properties of a Class A Amphipathic Helical Peptide," Journal of Lipid Research, 2001, pp. 1096-1104, vol. 42.

Homan, R. et al., "A fluorescence method to detect and quantitate sterol esterification by lecithin:cholesterol acyltransferase," Anal. Biochem., 2013, pp. 80-86, vol. 441.

Leman, L. J. et al., "Molecules That Mimic Apolipoprotein A?I: Potential Agents for Treating Atherosclerosis," J. Med. Chem., 2014, pp. 2169?2196, vol. 57. No. 6.

Uehara, Y. et al., "FAMP, a Novel ApoA-I Mimetic Peptide. Suppresses Aortic Plaque Formation Through Promotion of Biological HDL Function in ApoE-De?cient Mice," J Am Heart Assoc., 2013, pp. 1-16.

Yang, M. et al., "Efficient cytosolic delivery of siRNA using HDL-mimicking nanoparticles", Small, 2011, pp. 568-573, vol. 7, No. 5.

Zhang, Z.H. et al., "HDL-Mimicking Peptide-Lipid Nanoparticles with Improved Tumor Targeting", Small, pp. 430-437, vol. 6, No. 3, 2010.

Kuai, R. et al., "High-Denisty Lipoproteins: Nature's Multifunctional Nanoparticles," ACS Nano, 2016, pp. 3015-3041, vol. 10.

Qian F. et al., "Formation of Zinc-Peptide Spherical Micropartcies During Lyophilization from tert-Butyl Alcohol/Water Co-solvent System," Pharmaceutical Research, 2008, pp. 2799-2806, vol. 25, No. 12.

Simonsen, J. B., "Evaluation of reconstituted high-density lipoprotein (rHDL) as a drug delivery platform—a detailed survey of rHDL particles ranging from biophysical properties to clinical implication," Nanomedicine: Nanotechnology, Biology, and Medicine, 2016, pp. 2161-2179, vol. 12, No. 7.

Yang M. et al., "Attenuation of nontargeted cell-kill using a high-density lipoprotein-mimicking peptide-phospholipid nanoscaffoid," Nanomedicine, 2011, pp. 631-641, vol. 6, No. 4.

Yuan, Y. et al., "synthetic high-density lipoproteins for delivery; of 10-hydroxycamptothecin," International Journal of Nanomedicine, 2016, pp. 6229-6238, vol. 11.

Zheng, Z.H. et al, "Biomimetic nanocarrier for direct cytosolic drug delivery", Angew Chem Int Ed, 2009, pp. 9171-9175, vol. 48.

Balzeau, J. et al., "The effect of fuctionalizing lipid nanocapsules with NFL-TBS.40-63 peptide on their uptake by gliobalstoma cells," Biomaterials, 2013, pp. 3381-3389, vol. 34, No. 13.

European Search Report for Application Serial No. 16824940.7 dated Jan. 15, 2019, 3 pages.

Zhang, Z.H. et al., "HDL-Mimicking Peptide-Lipid Nanoparticles with Improved Tumor Targeting", Small, vol. 6, No. 3, 2010, pp. 430-437.

FIG. 1A
SEQ ID NO: 3
FIG. 1B
SEQ ID NO: 25
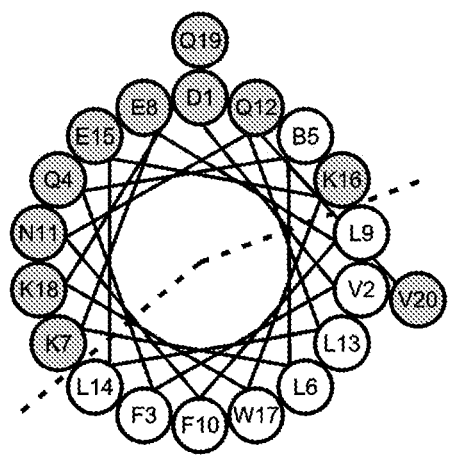
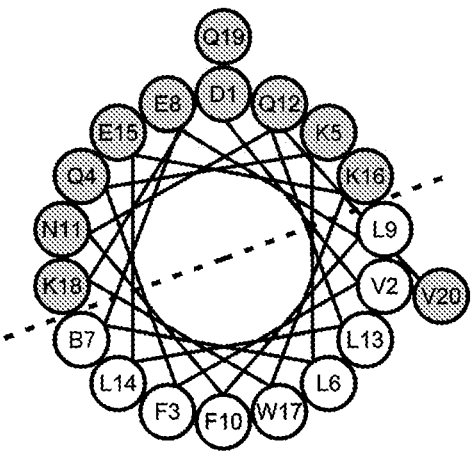
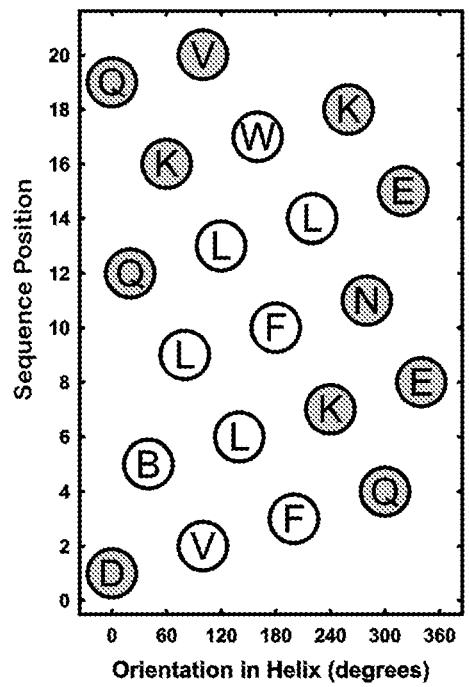
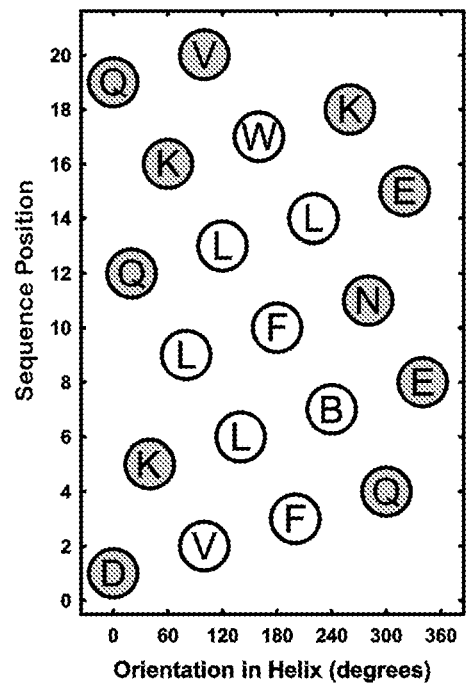
FIG. 1C
FIG. 1D

FORMULATIONS FOR IMPROVING THE EFFICACY OF HYDROPHOBIC DRUGS

CROSS REFERENCE TO RELATED APPLICATIONS

This application a 371 of International Application of, PCT/US2016/041544, filed Jul. 8, 2016, which claims the benefit under 35 USC § 119 of U.S. Provisional Application No. 62/190,909, filed Jul. 10, 2015, the entire contents of the aforementioned disclosures are hereby incorporated by reference herein.

SEQUENCE LISTING

This application incorporates by reference in its entirety the sequence listing entitled "236603-397087_Corrected_Sequence_Listing_ST25.txt" created on Jan. 29, 2018, at 2:29 pm, that is 29 KB, and filed electronically herewith.

FIELD

The present invention relates to the transport and delivery of therapeutic molecules to their sites of action via parenteral administration. More particularly, the present invention concerns a formulation technology enabling the incorporation of drugs into nanoparticles that can be readily administered parenterally for the safe and effective delivery of the incorporated drugs to their therapeutic targets.

BACKGROUND

Many therapeutic substances that operate systemically are not suitable for the relative simplicity of oral dosing and must be administered parenterally instead. However, often the same factors that complicate oral dosing impede the parenteral dosing process. Such factors include poor water solubility due to hydrophobicity or other properties, drug instability in the digestive tract, insufficient absorption or enhanced clearance after absorption, resulting in inadequate plasma concentrations and/or exposure times.

Options for dealing with hydrophobic drugs requiring parenteral dosing usually involve the addition of various excipients to obtain stable suspensions, dispersions or solutions suitable for injection. The types of excipients used include detergents, polymers of various types, oil emulsions, phospholipids and albumin. In many cases the excipients used to obtain the necessary drug solubilization are detergent-like substances. These include deoxycholate; Cremophor EL®, a polyethyloxated derivative of castor oil; and polysorbate 80. The latter two are typically used in tandem with ethanol. These agents solve the solubilization problem but they have noxious properties which introduce a high risk of hypersensitivity reactions. It is a common requirement that patients injected with solutions containing Cremophore EL® or polysorbate 80 are pretreated with anti-inflammatory drugs to subdue formulation-dependent inflammation. The most serious consequences of hypersensitivity reactions are reduced tolerance to treatment and increased risk of death.

Examples of approved drug formulations containing Cremophore EL® or polysorbate 80 for solubilization include the hydrophobic anti-cancer drugs paclitaxel (Taxol®), docetaxel (Taxotere®), cabazitaxel (Jevtana®) and ixabepilone (Ixempra®). The immnuosuppresants cyclosporine (Sandimmune®), tacrolimus (Prograf®) and temsirolimus (Torisel®) also depend on these agents for formulation. In the case of paclitaxel, some progress has been made through the substitution of albumin for Cremophore EL® and ethanol as a dispersing agent (i.e. Abraxane®). The antifungal agent amphotericin B is also quite hydrophobic and requires measures to obtain a stable suspension for infusion.

Other dosing hurdles many drugs face include rapid clearance and inactivation by metabolic pathways. For example, the anti-cancer agent gemcitabine must be infused at high doses to overwhelm its breakdown by cytidine deaminase in order to obtain therapeutic levels. A further problem limiting drug administration is unintended exposure of non-target tissues to the effects of those drugs. This is particularly significant for cytotoxic anti-cancer drugs.

Descriptions of attempts to discover superior parenteral formulations including emulsions, micelles, liposomal formulations, polymers, and solid-lipid nanoparticles, are numerous but many efforts have been hindered by problems of low entrapment efficiency, drug instability, payload leakage and poor storage stability. Some success has been obtained with liposomal formulations. Examples include cytarabine in liposomes (DepoCyt®) to reduce clearance rates, doxorubicin in liposomes (Doxil®, Myocet®) to reduce cardiotoxicity, and amphotericin-B in liposomes (e.g. AmBisome®) to improve solubilization.

Given the limited number of current treatments, and inadequacy of options, there is a clear need to provide formulation alternatives for parenterally administered drugs with improved safety profiles and therapeutic indexes; and/or therapies which at least provide the public with a useful choice.

SUMMARY

The present disclosure addresses this need by providing novel nanoparticle formulations of lipid and peptide and methods to form them that allow incorporation of molecules, e.g., drugs and are stable in infusion or injection solutions. The formulations of the invention provide one or more improvements, including but not limited to, improved pharmacokinetic parameters, increased half-life, targeted delivery, diminished toxicity or an improved therapeutic index for parenterally-administered drugs, in particular, anti-cancer drugs.

The present disclosure provides amphiphilic, alpha-helical peptides that comprise an amino acid sequence of SEQ ID NO:1, SEQ ID NO:24, SEQ ID NO:36 or SEQ ID NO:59.

Further, the present disclosure provides peptide amphiphile lipid micelles (PALM) which comprise a peptide comprising an amino acid sequence of the disclosure, sphingomyelin and one or more additional phospholipids. The PALM of the present disclosure optionally comprise one or more cargo molecules, such as imaging agents and drugs.

The present disclosure also provides for processes for preparing PALM and PALM composition formulated with cargo molecules.

Additionally the present disclosure provides for compound conjugates and methods of preparing compound conjugates suitable for use with PALM.

Further the present disclosure provides for methods of treating disorders by administering PALM-drug conjugates.

BRIEF DESCRIPTION OF THE FIGURES

FIGS. 1A and 1B are Edmundson Wheel depictions of the peptides of SEQ ID NOs: 3 and 25 respectively showing their amphiphilic conformation. FIGS. 1A and 1B further show the axial positions of the constituent amino acids (identified by standard single letter abbreviations) around the long axis of the alpha-helix. The letter "B" represents 2-amino-isobutyric acid. The dashed lines indicate the approximate boundaries between hydrophilic amino acids (shaded) forming the polar faces of the peptides and the hydrophobic amino acids forming the non-polar faces. FIGS. 1C and 1D are helical net depictions of the peptides of SEQ ID NOs: 3 and 25 respectively.

DETAILED DESCRIPTION

Definitions

Figure 2:
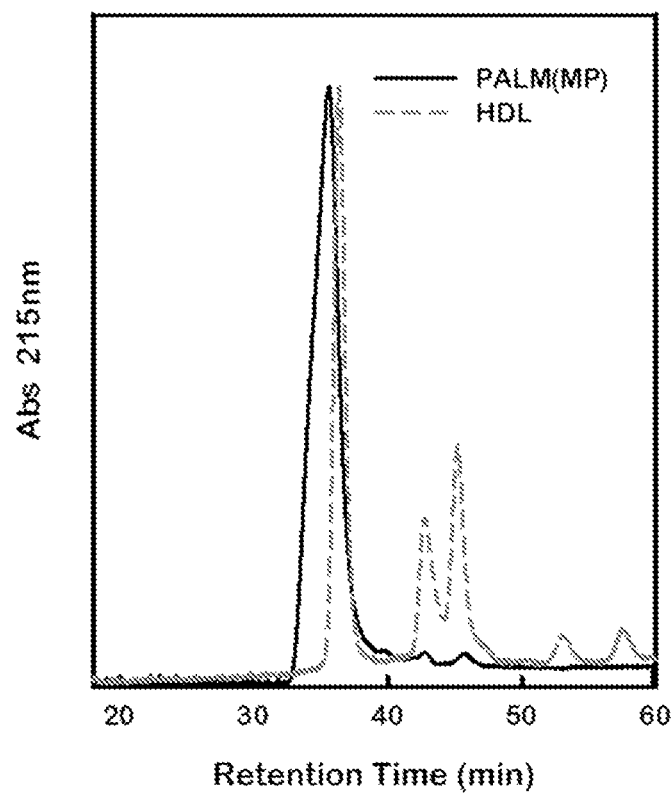
FIG. 2. The size exclusion chromatogram of PALM containing miriplatin (solid line) compared to human HDL (dashed line). PALM was composed of peptide of SEQ ID NO:25 and POPC, SM and miriplatin at a 2.5:3:7:0.75 mole ratio.

"Nanoparticle" means a particle having no dimension greater than 100 nm.

As used herein, the singular forms "a", "an" and "the" include plural references unless the context clearly dictates otherwise.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

The antecedent "about" indicates that the values are approximate. For example the range of "about 1 mg to about 50 mg" indicates that the values are approximate values. The range of "about 1 mg to about 50 mg" includes approximate and specific values, e.g., the range includes about 1 mg, 1 mg, about 50 mg and 50 mg.

When a range is described, the range includes both the endpoints of the range as well as all numbers in between. For example, "between 1 mg and 10 mg" includes 1 mg, 10 mg and all amounts between 1 mg and 10 mg. Likewise, "from 1 mg to 10 mg" includes 1 mg, 10 mg and all amounts between 1 mg and 10 mg.

As used herein, "alkyl" refers to a saturated aliphatic hydrocarbon group containing from 7-21 carbon atoms. As used herein, the terminology ($C_1$-$C_n$) alkyl refers to an alkyl group containing 1-n carbon atoms. For example, ($C_8$-$C_{12}$) alkyl refers to an alkyl group containing 8, 9, 10, 11, or 12 carbon atoms. An alkyl group can be branched or unbranched.

As used herein, "alkenyl" refers to an aliphatic carbon group that contains from 7-21 carbon atoms and at least one double bond. As used herein, the terminology ($C_1$-$C_n$) alkenyl refers to an alkenyl group containing 1-n carbon atoms. An alkenyl group can be branched or unbranched.

"Consisting essentially of" when used to describe the lipid component means that the lipid component includes less than 0.1 mol % of any additional lipid other than those specified.

"XC" is an abbreviation for paclitaxel 2'-cholesteryl carbonate.

XT3 is an abbreviation for paclitaxel 2'-6-tocotrienyl carbonate.

"MP" is an abbreviation for miriplatin.

"PTX" is an abbreviation for paclitaxel

"POPC" is an abbreviation for 1-palmitoyl-2-oleoyl phosphatidylcholine

"SM" is an abbreviation for sphingomyelin

"HDL" is an abbreviation for high density lipoprotein.

"SR-BI" is an abbreviation for scavenger receptor class B, type 1.

"BHK" is an abbreviation for baby hamster kidney.

"DiI" is an abbreviation for 1,1'-dioctadecyl-3,3,3',3'-tetramethylindocarbocyanine "PALM" is an acronym used to identify the peptide amphiphile lipid micelles formed from a combination of amphiphilic peptide with phospholipids and optionally other hydrophobic molecules, in aqueous suspension.

"Amphiphilic" describes a molecule or polymer (e.g. peptide) with affinity for both lipid and aqueous phases due to a conformation in which hydrophilic (water seeking) substituents and hydrophobic (water avoiding) substituents in the molecule or polymer are structurally segregated from one another.

"Lipophilic" describes a substance that distributes preferentially to lipid domains of lipid-rich particles in aqueous suspension. The lipid-rich particles include lipid micelles, liposomes, lipoproteins, cell membranes and lipid emulsions.

"Peptide" is a polymer produced from alpha-amino acid monomers joined together by amide bonds formed between the carboxylic group of one amino acid and the alpha-amine group of the next amino acid in the polymer. "Peptide" also includes a polymer of amino acid monomers joined together. Both L-optical isomers and the D-optical isomers of amino acids can be used. Amino acids making up the polymer may be either those found in nature (i.e. natural amino acids) or un-natural amino acids. The term "residue" or "amino acid residue" includes reference to an amino acid that is incorporated into a peptide, polypeptide, or protein.

Peptide sequences according to convention, and as used herein, are written N-terminus to C-terminus, left to right.

"Micelle" is a multi-molecular structure organized by non-covalent interactions in an aqueous phase. The micelle is composed of amphiphilic and hydrophobic molecules which aggregate in such a manner that the hydrophobic domains of molecules are shielded from the water and the hydrophilic constituents are at the micelle-water interface.

"Cargo molecules" are hydrophobic or amphiphilic molecules with pharmaceutical, therapeutic or diagnostic properties that are stably incorporated into PALM and do not disrupt the stability of PALM.

"siRNA" are small, interfering ribonucleic acids created to control cellular gene expression as part of the RNA-induced gene silencing complex.

"Aib" is the three letter code for the amino acid alpha-amino isobutyric acid.

"Aba" is the three letter code for the amino acid alpha-amino butyric acid.

"Amv" is the three letter code for the unnatural amino acid alpha-methyl valine.

"Orn" is the three letter code for the amino acid ornithine.

"SEC" is size exclusion chromatography

"DLS" is dynamic light scattering

A first aspect of the present disclosure provides "amphiphilic peptides". Amphiphilic peptides are able to adopt an alpha helical conformation in which the helix has opposing polar and non-polar faces oriented along the long axis of the helix. Techniques of synthesizing peptides are well known in the art. The peptides of the present disclosure can be synthesized by any technique known in the art.

Table 1 shows the charge distribution of specific amphiphilic peptides of the present disclosure compared with several prior art sequences. The charge distribution of the peptides of the present invention are novel in view of the prior art shown below.

TABLE 1

| | | Charges of Residues in Apolipoprotein A-I Mimetic Peptides at Neutral pH | | | | | | | | | | | | | | | | | | | | | | | |
|---|---|---|---|---|---|---|---|---|---|---|---|---|---|---|---|---|---|---|---|---|---|---|---|---|---|
| | N-Term | Amino Acid Position | | | | | | | | | | | | | | | | | | | | | | | C-Term |
| Peptide | Charge | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | Charge |
| SEQ ID[a] | + | − | o | o | o | o | o | + | − | o | o | o | o | o | o | − | + | o | + | o | o | | | | | − |
| SEQ ID[b] | + | − | o | o | o | + | o | o | − | o | o | o | o | o | o | − | + | o | + | o | o | | | | | − |
| A-I$_{con}$[c] | + | o | o | o | − | − | o | + | o | + | o | o | − | o | o | − | o | o | + | o | + | o | + | | | − |
| LAP642[d] | + | o | o | o | − | o | o | + | − | o | o | o | − | o | o | − | o | o | + | o | + | o | + | | | − |
| 18A[e] | + | − | o | o | + | o | o | o | − | + | o | o | − | + | o | + | − | o | o | | | | | | | − |
| 2F[f] | o | − | o | o | + | o | o | o | − | + | o | o | − | + | o | + | − | o | o | | | | | | | o |
| R4F[g] | o | o | o | − | + | o | + | − | o | o | + | − | o | o | o | + | o | o | − | | | | | | | o |
| FAMP[h] | + | o | o | − | o | o | o | o | o | o | − | + | o | o | + | o | o | − | − | o | o | + | + | o | o | − |

[a]SEQ ID NOs: 1-23
[b]SEQ ID NOs: 24-35
[c]Anantharamaiah et al. (1990) Arteriosclerosis 10: 95-105
[d]Homan et al. (2013) Anal. Biochem. 441: 80-86
[e]Anantharamaiah et al. (1985) J. Biol. Chem. 260: 10248-10255
[f]Datta et al. (2001) J. Lipid Res. 42: 1096-1104
[g]Zhang et al. (2009) Angew. Chem. Int. Ed. 48: 9171-9175
[h]Uehara et al. (2013) J Am Heart Assoc. 2(3): e000048. doi: 10.1161/JAHA.113.000048
"o" indicates zero charge at the indicated position.
"+" indicates a positive charge at the indicated position.
"−" indicates a negative charge at the indicated position.

One embodiment of the first aspect of the disclosure provides a peptide that comprises the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$ wherein: $X_1$ is the amino acid D; $X_2$ and $X_{20}$ are each the amino acid V; $X_3$, $X_6$, $X_{10}$ and $X_{13}$ are each an amino acid independently selected from the group consisting of L and F; $X_4$, $X_{12}$ and $X_{19}$ are each the amino acid Q; $X_5$ is the amino acid A or Aib; $X_7$, $X_{16}$ and $X_{18}$ are each the amino acid K; $X_8$ and $X_{15}$ are each the amino acid E; $X_9$ and $X_{14}$ are each an amino acid independently selected from the group consisting of A, L, F and Aib; $X_{11}$ is an amino acid selected from the group consisting of A, Aib and N; and $X_{17}$ is an amino acid selected from the group consisting of W, F and L, (SEQ ID NO:1) wherein the peptide is from 20 to 24 amino acids in length.

Another embodiment of the first aspect provides a peptide that consists essentially of the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$ wherein: $X_1$ is the amino acid D; $X_2$ and $X_{20}$ are each the amino acid V; $X_3$, $X_6$, $X_{10}$ and $X_{13}$ are each an amino acid independently selected from the group consisting of L and F; $X_4$, $X_{12}$ and $X_{19}$ are each the amino acid Q; $X_5$ is the amino acid A or Aib; $X_7$, $X_{16}$ and $X_{18}$ are each the amino acid K; $X_8$ and $X_{15}$ are each the amino acid E; $X_9$ and $X_{14}$ are each an amino acid independently selected from the group consisting of A, L, F and Aib; $X_{11}$ is an amino acid selected from the group consisting of A, Aib and N; and $X_{17}$ is an amino acid selected from the group consisting of W, F and L, (SEQ ID NO:1) wherein the peptide is from 20 to 24 amino acids in length.

Still another embodiment of the first aspect provides a peptide that consists of the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$ wherein: $X_1$ is the amino acid D; $X_2$ and $X_{20}$ are each the amino acid V; $X_3$, $X_6$, $X_{10}$ and $X_{13}$ are each an amino acid independently selected from the group consisting of L and F; $X_4$, $X_{12}$ and $X_{19}$ are each the amino acid Q; $X_5$ is the amino acid A or Aib; $X_7$, $X_{16}$ and $X_{18}$ are each the amino acid K; $X_8$ and $X_{15}$ are each the amino acid E; $X_9$ and $X_{14}$ are each an amino acid independently selected from the group consisting of A, L, F and Aib; $X_{11}$ is an amino acid selected from the group consisting of A, Aib and N; and $X_{17}$ is an amino acid selected from the group consisting of W, F and L. (SEQ ID NO:1)

Yet another embodiment of the first aspect provides a peptide that comprises the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$ wherein: $X_1$, $X_8$ and $X_{15}$ are independently selected from the group consisting of the amino acids D and E; $X_2$ and $X_{20}$ are each an amino acid independently selected from the group consisting of V, I, and L; $X_3$, $X_6$, $X_{10}$ and $X_{13}$, is an amino acid selected from the group consisting of L, I, V, W, Y, Aib, Amv and F; $X_4$, $X_{12}$ and $X_{19}$ are each an amino acid independently selected from the group consisting of Q and N; $X_5$, $X_{16}$ and $X_{18}$ are each an amino acid independently selected from the group consisting of K, R, H and Orn; $X_7$ is an amino acid selected from the group consisting of A, G, S, V, Amv and Aib; $X_9$ and $X_{14}$ are an amino acid are independently selected from the group consisting of A, G, S, L, F, V, Amv and Aib; and $X_{11}$ is an amino acid selected from the group consisting of A, G, S, Aib, Amv, V and N; and $X_{17}$ is an amino acid selected from the group consisting of W, F, Y, I, V, and L, (SEQ ID NO:24) wherein the peptide is from 20 to 24 amino acids in length.

Another embodiment of the first aspect provides a peptide that consists essentially of the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$ wherein: $X_1$, $X_8$ and $X_{15}$ are each an amino acid selected from the group consisting of D and E; $X_2$ and $X_{20}$ are each an amino acid independently selected from the group consisting of V, I, and L; $X_3$, $X_6$, $X_{10}$ and $X_{13}$ are each an amino acid independently selected from the group consisting of L, I, V, W, Y, Aib, Amv and F; $X_4$, $X_{12}$ and $X_{19}$ are each an amino acid independently selected from the group consisting of Q and N; $X_5$, $X_{16}$ and $X_{18}$ are each an amino acid independently selected from the group consisting of K, R, H and Orn; $X_7$ is an amino acid selected from the group consisting of A, G, S, V, Aib and Amv, $X_9$ and $X_{14}$ are an amino acid independently selected from the group consisting of A, G, S, L, F, V, Amv, and Aib; $X_{11}$ is an amino acid selected from the group consisting of A, G, S, Aib, Amv, V and N; and $X_{17}$ is an amino acid selected from the group consisting of W, F, Y, I, V, and L, (SEQ ID NO:24) and the peptide is from 20 to 24 amino acids in length.

Still another embodiment of the first aspect provides a peptide that consists of the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$ wherein: $X_1$, $X_8$ and $X_{15}$ are each an amino acid selected from the group consisting of D and E; $X_2$ and $X_{20}$ are each an amino acid independently selected from the group consisting of V, I, and L; $X_3$, $X_6$, $X_{10}$ and $X_{13}$ are each an amino acid independently selected from the group consisting of L, I, V, W, Y, Aib, Amv and F; $X_4$, $X_{12}$ and $X_{19}$ are each an amino acid independently selected from the group consisting of Q and N; $X_5$, $X_{16}$ and $X_{18}$ are each an amino acid independently selected from the group consisting of K, R, H and Orn; $X_7$ is an amino acid selected from the group consisting of A, G, S, V, Aib and Amv, $X_9$ and $X_{14}$ are an amino acid independently selected from the group consisting of A, G, S, L, F, V, Amv, and Aib; $X_{11}$ is an amino acid selected from the group consisting of A, G, S, Aib, Amv, V and N; and $X_{17}$ is an amino acid selected from the group consisting of W, F, Y, I, V, and L. (SEQ ID NO:24)

It is contemplated that any of the disclosed embodiments of the peptides according to the first aspect are optionally acylated at the alpha-amine of the N-terminal amino acid of the peptide, optionally amidated at the terminal carboxyl group of the peptide, or optionally acylated at the alpha-amine of the N-terminal amino acid and amidated at the terminal carboxyl group of the peptide. Peptides can be acylated or amidated by methods known in the art.

Particular peptides of the present invention are provided in Table 2 below.

TABLE 2

| SEQ ID NO: | Peptide Sequence | Mean Hydrophobic Moment [a] | Mean Hydrophobicity [b] |
|---|---|---|---|
| 2 | DVFQALKELFAQLLEKWKQV | 0.846 | -1.043 |
| 3 | DVFQ{AIB}LKELFNQLLEKWKQV | 0.908 | -1.135 |
| 4 | DVFQ{AIB}LKELLAQLLEKFKQV | 0.885 | -0.995 |
| 5 | DVFQ{AIB}LKELLNQLLEKFKQV | 0.948 | -1.092 |
| 6 | DVFQ{AIB}LKELLNQL{AIB}EKFKQV | 0.940 | -1.120 |
| 7 | DVFQ{AIB}LKELLNQL{AIB}EKWKQV | 0.910 | -1.151 |
| 8 | DVFQALKELLAQLLEKFKQV | 0.887 | -1.000 |
| 9 | DVFQALKELLNQLLEKFKQV | 0.950 | -1.097 |
| 10 | DVFQ{AIB}LKELFAQLLEKWKQV | 0.845 | -1.038 |
| 11 | DVFQ{AIB}LKELFNQLLEKWKQV | 0.908 | -1.135 |
| 12 | DVFQ{AIB}LKELFNQLLEKFKQV | 0.938 | -1.104 |
| 13 | DVFQALKELFAQL{AIB}EKWKQV | 0.836 | -1.071 |
| 14 | DVFQALKELFNQL{AIB}EKWKQV | 0.902 | -1.168 |
| 15 | DVFQALKELFNQL{AIB}EKFKQV | 0.932 | -1.137 |
| 16 | DVFQAFKEAFAQLFEKWKQV | 0.821 | -1.099 |
| 17 | DVFQAFKE{AIB}FAQLFEKWKQV | 0.822 | -1.094 |
| 18 | DVFQ{AIB}FKE{AIB}FAQLFEKWKQV | 0.820 | -1.089 |
| 19 | DVFQAFKEAF{AIB}QLFEKWKQV | 0.818 | -1.094 |
| 20 | DVFQAFKE{AIB}F{AIB}QLFEKWKQV | 0.819 | -1.089 |
| 21 | DVFQ{AIB}FKE{AIB}F{AIB}QLFEKWKQV | 0.817 | -1.084 |
| 22 | DVFQALKELFNQLLEKWKQV | 0.910 | -1.140 |
| 23 | DVFQ{AIB}LKELLNQLLEKLKQV | 0.959 | -1.081 |
| 25 | DVFQKL{AIB}ELFNQLLEKWKQV | 0.976 | -1.135 |
| 26 | DVFQKLVELFNQLLEKWKQV | 0.979 | -1.119 |
| 27 | DV{AIB}QKLFELFNQLLEKWKQV | 0.966 | -1.135 |
| 28 | DVFQKL{AIB}ELFNQLLEKFKQV | 1.007 | -1.104 |
| 29 | DVFQKLVELFNQLLEKFKQV | 1.010 | -1.088 |

TABLE 2-continued

| SEQ ID NO: | Peptide Sequence | Mean Hydro- phobic Moment [a] | Mean Hydro- phobi- city [b] |
|---|---|---|---|
| 30 | DV{AIB}QKLFELFNQLLEKFKQV | 0.997 | −1.104 |
| 31 | DVLQKF{AIB}ELFNQLLEKWKQV | 0.974 | −1.135 |
| 32 | DV{AIB}QKFLELFNQLLEKWKQV | 0.958 | −1.135 |
| 33 | DVFQKLLE{AIB}FNQLLEKWKQV | 0.979 | −1.135 |
| 34 | DVFQKL{AIB}ELFNQ{AIB}LEKWKQV | 0.955 | −1.163 |
| 35 | DVFQKL{AIB}ELFNQL{AIB}EKWKQV | 0.961 | −1.163 |

[a] Calculated from amino acid hydrophobicity (Hessa et al. Nature 433: 377-381 (2005)) according to Pownall et al. (FEBS Letters159: 17-23 (1983)).
[b] Calculated as the sum of amino acid hydrophobicities divided by the number of residues (kcal/mol/residue).

One embodiment of the first aspect of the disclosure is a peptide comprising any one of the amino acid sequences of SEQ ID NOs:1-23 where the peptide is from 20 to 24 amino acids in length. Yet another embodiment is a peptide consisting essentially of any one of the amino acid sequences of SEQ ID NOs: 1-23 where the peptide is from 20 to 24 amino acids in length. Yet another embodiment is a peptide consisting of any one of the amino acid sequences of SEQ ID NOs: 1-23. In any of the above embodiments of the disclosed peptides, optionally the alpha-amine of the N-terminal amino acid of the peptide is acylated; the terminal carboxyl group is amidated; or the alpha-amine of the N-terminal amino acid is acylated and the terminal carboxyl group of the peptide is amidated.

One embodiment of the first aspect of the disclosure is a peptide comprising any one of the amino acid sequences of SEQ ID NOs:25-35 where the peptide is from 20 to 24 amino acids in length. Still another embodiment is a peptide consisting essentially of any one of the amino acid sequences of SEQ ID NOs: 25-35 where the peptide is from 20 to 24 amino acids in length. Another embodiment is a peptide consisting of any one of the amino acid sequences of SEQ ID NOs: 25-35. In any of the above embodiments of the peptides, optionally the alpha-amine of the N-terminal amino acid of the peptide is acylated; the terminal carboxyl group is amidated; or the alpha-amine of the N-terminal amino acid is acylated and the terminal carboxyl group of the peptide is amidated.

Embodiments of the present disclosure further include peptides that have the reverse sequence of the peptides generically defined by SEQ ID NOs: 1 and 24.

One embodiment of the first aspect of the disclosure provides peptides that are the reverse of SEQ ID NO:1 and the peptides comprise the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$, wherein $X_1$ and $X_{19}$ are each the amino acid V; $X_2$, $X_9$ and $X_{17}$ are each the amino acid Q; $X_3$, $X_5$ and $X_{14}$ are each the amino acid K; $X_4$ is an amino acid selected from the group consisting of W, F, and L; $X_6$ and $X_{13}$ are each the amino acid E; $X_7$ and $X_{12}$ are each an amino acid independently selected from the group consisting of A, L, F, and Aib; $X_8$, $X_{11}$, $X_{15}$ and $X_{18}$ are each an amino acid independently selected from the group consisting of L and F; $X_{10}$ is an amino acid selected from the group consisting of A, Aib and N; $X_{16}$ is an amino acid selected from the group consisting of A and Aib; and $X_{20}$ is the amino acid D, (SEQ ID NO:36) wherein the peptide is from 20 to 24 amino acids in length.

Another embodiment of the first aspect of the disclosure provides peptides that are the reverse of SEQ ID NO:1 and the peptides comprise the amino acid sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$, wherein $X_1$ and $X_{19}$ are each the amino acid $X_2$, $X_9$ and $X_{17}$ are each the amino acid Q; $X_3$, $X_5$ and $X_{14}$ are each the amino acid K; $X_4$ is an amino acid selected from the group consisting of W, F, and L; $X_6$ and $X_{13}$ are each the amino acid E; $X_7$ and $X_{12}$ are each an amino acid independently selected from the group consisting of A, L, F, and Aib; $X_8$, $X_{11}$, $X_{15}$ and $X_{18}$ are each an amino acid independently selected from the group consisting of L and F; $X_{10}$ is an amino acid selected from the group consisting of A, Aib and N; $X_{16}$ is an amino acid selected from the group consisting of A and Aib; and $X_{20}$ is the amino acid D, (SEQ ID NO:36) wherein the peptide is from 20 to 24 amino acids in length.

One embodiment of the first aspect of the disclosure provides peptides that are the reverse of SEQ ID NO:1 and the peptides consist of the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$, wherein $X_1$ and $X_{19}$ are each the amino acid V; $X_2$, $X_9$ and $X_{17}$ are each the amino acid Q; $X_3$, $X_5$ and $X_{14}$ are each the amino acid K; $X_4$ is an amino acid selected from the group consisting of W, F, and L; $X_6$ and $X_{13}$ are each the amino acid E; $X_7$ and $X_{12}$ are each an amino acid independently selected from the group consisting of A, L, F, and Aib; $X_8$, $X_{11}$, $X_{15}$ and $X_{18}$ are each an amino acid independently selected from the group consisting of L and F; $X_{10}$ is an amino acid selected from the group consisting of A, Aib and N; $X_{16}$ is an amino acid selected from the group consisting of A and Aib; and $X_{20}$ is the amino acid D. (SEQ ID NO:36)

Another embodiment of the first aspect of the disclosure provides peptides that are the reverse of SEQ ID NO:24 and the reverse peptides comprise the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$ wherein $X_1$ and $X_{19}$ are each an amino acid independently selected from the group consisting of V, I and L; $X_2$, $X_9$ and $X_{17}$ are each an amino acid independently selected from the group consisting of Q and N; $X_3$, $X_5$ and $X_{16}$ are each an amino acid independently selected from the group consisting of K, R, H, and Orn; $X_4$ is an amino acid selected from the group consisting of W, F, Y, I, V, and L; $X_6$, $X_{13}$ and $X_{20}$ are each an amino acid independently selected from the group consisting of E and D; $X_7$ and $X_{12}$ are each an amino acid independently selected from the group consisting of A, G, S, L, F, V, Amv and Aib; $X_8$, $X_{11}$, $X_{15}$ and $X_{18}$ are independently selected from the group consisting of the amino acid L, I, V, W, Aib, Amv and F; $X_{10}$ is an amino acid selected from the group consisting of A, G, S, Aib, Amv, V and N; and $X_{14}$ is an amino acid selected from the group consisting of A, G, S, V, Aib and Amv, (SEQ ID NO:59) wherein the peptide is from 20 to 24 amino acids in length.

Another embodiment of the first aspect of the disclosure provides peptides that are the reverse of SEQ ID NO:24 and the reverse peptides consist essentially of the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$ wherein $X_1$ and $X_{19}$ are each an amino acid independently selected from the group consisting of V, I and L; $X_2$, $X_9$ and $X_{17}$ are each an amino acid independently selected from the group consisting of Q and N; $X_3$, $X_5$ and $X_{16}$ are each an amino acid independently selected from the group consisting of K, R, H, and Orn; $X_4$ is an amino acid selected from the group consisting of W, F, Y, I, V, and L; $X_6$, $X_{13}$ and $X_{20}$ are each an amino acid independently selected from the group consisting of E and D; $X_7$ and $X_{12}$ are each an amino acid independently selected from the group consisting of A, G, S, L, F, V, Amv and Aib; $X_8$, $X_{11}$, $X_{15}$ and $X_{18}$ are independently selected from the group consisting of the amino acid L, I, V, W, Aib, Amv and F; $X_{10}$ is an amino acid selected from the group consisting of A, G, S, Aib, Amv, V and N; and $X_{14}$ is an amino acid selected from the group consisting of A, G, S, V, Aib and Amv, (SEQ ID NO:59) wherein the peptide is from 20 to 24 amino acids in length.

Another embodiment of the first aspect of the disclosure provides peptides that are the reverse of SEQ ID NO:24 and the reverse peptides consist of the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$ wherein $X_1$ and $X_{19}$ are each an amino acid independently selected from the group consisting of V, I and L; $X_2$, $X_9$ and $X_{17}$ are each an amino acid independently selected from the group consisting of Q and N; $X_3$, $X_5$ and $X_{16}$ are each an amino acid independently selected from the group consisting of K, R, H, and Orn; $X_4$ is an amino acid selected from the group consisting of W, F, Y, I, V, and L; $X_6$, $X_{13}$ and $X_{20}$ are each an amino acid independently selected from the group consisting of E and D; $X_7$ and $X_{12}$ are each an amino acid independently selected from the group consisting of A, G, S, L, F, V, Amv and Aib; $X_8$, $X_{11}$, $X_{15}$ and $X_{18}$ are independently selected from the group consisting of the amino acid L, I, V, W, Aib, Amv and F; $X_{10}$ is an amino acid selected from the group consisting of A, G, S, Aib, Amv, V and N; and $X_{14}$ is an amino acid selected from the group consisting of A, G, S, V, Aib and Amv. (SEQ ID NO:59)

Provided in Table 3 are additional peptides of the present invention. The sequences of the amino acids in these peptides are the reverse of the amino acid sequences of SEQ ID NOs:2-23 and 25-35.

TABLE 3

| SEQ ID NO: | Peptide Sequence |
|---|---|
| 37 | VQKWKELLQAFLEKLAQFVD |
| 38 | VQKWKELLQNFLEKL{AIB}QFVD |
| 39 | VQKFKELLQALLEKL{AIB}QFVD |
| 40 | VQKFKELLQNLLEKL{AIB}QFVD |
| 41 | VQKFKE{AIB}LQNLLEKL{AIB}QFVD |
| 42 | VQKWKE{AIB}LQNLLEKL{AIB}QFVD |
| 43 | VQKFKELLQALLEKLAQFVD |
| 44 | VQKFKELLQNLLEKLAQFVD |
| 45 | VQKWKELLQAFLEKL{AIB}QFVD |
| 46 | VQKWKELLQNFLEKL{AIB}QFVD |
| 47 | VQKFKELLQNFLEKL{AIB}QFVD |
| 48 | VQKWKE{AIB}LQAFLEKLAQFVD |
| 49 | VQKWKE{AIB}LQNFLEKLAQFVD |
| 50 | VQKFKE{AIB}LQNFLEKLAQFVD |
| 51 | VQKWKEFLQAFAEKFAQFVD |
| 52 | VQKWKEFLQAF{AIB}EKFAQFVD |
| 53 | VQKWKEFLQAF{AIB}EKF{AIB}QFVD |
| 54 | VQKWKEFLQ{AIB}FAEKFAQFVD |
| 55 | VQKWKEFLQ{AIB}F{AIB}EKFAQFVD |
| 56 | VQKWKEFLQ{AIB}F{AIB}EKF{AIB}QFVD |
| 57 | VQKWKELLQNFLEKLAQFVD |
| 58 | VQKLKELLQNLLEKL{AIB}QFVD |
| 60 | VQKWKELLQNFLE{AIB}LKQFVD |
| 61 | VQKWKELLQNFLEVLKQFVD |
| 62 | VQKWKELLQNFLEFLKQ{AIB}VD |
| 63 | VQKFKELLQNFLE{AIB}LKQFVD |
| 64 | VQKFKELLQNFLEVLKQFVD |
| 65 | VQKFKELLQNFLEFLKQ{AIB}VD |
| 66 | VQKWKELLQNFLE{AIB}FKQLVD |
| 67 | VQKWKELLQNFLELFKQ{AIB}VD |
| 68 | VQKWKELLQNF{AIB}ELLKQFVD |
| 69 | VQKWKEL{AIB}QNFLE{AIB}LKQFVD |
| 70 | VQKWKE{AIB}LQNFLE{AIB}LKQFVD |

One embodiment of the first aspect of the disclosure is a peptide comprising any one of the amino acid sequences of SEQ ID NOs:36-58 where the peptide is from 20 to 24 amino acids in length. Yet another embodiment is a peptide consisting essentially of any one of the amino acid sequences of SEQ ID NOs: 36-58. Yet another embodiment is a peptide consisting of any one of the amino acid sequences of SEQ ID NOs: 36-58. In any of the above embodiments of the peptides, optionally the alpha-amine of the N-terminal amino acid of the peptide is acylated; the terminal carboxyl group is amidated; or the alpha-amine of the N-terminal amino acid is acylated and the terminal carboxyl group of the peptide is amidated.

One embodiment of the first aspect of the disclosure is a peptide comprising any one of the amino acid sequences of SEQ ID NOs: 59-70 where the peptide is from 20 to 24 amino acids in length. Still another embodiment is a peptide consisting essentially of any one of the amino acid sequences of SEQ ID NOs: 59-70. Yet another embodiment is a peptide consisting of any one of the amino acid sequences of SEQ ID NOs: 59-70. In any of the above embodiments of the peptides, optionally the alpha-amine of the N-terminal amino acid of the peptide is acylated; the terminal carboxyl group is amidated; or the alpha-amine of the N-terminal amino acid is acylated and the terminal carboxyl group of the peptide is amidated.

Where a peptide of the disclosure comprises an amino acid sequence of any one of SEQ ID NOs: 1-70 and from 1-4 additional amino independently added to either the N-terminus or C-terminus of the amino acid sequence, the additional amino acids are selected such that the addition of the amino acids does not negatively affect the amphilicity of the peptide.

A second aspect of the disclosure provides peptide amphiphile lipid micelles (PALM) formed from a combination of amphiphilic peptide with phospholipids. PALM of the second aspect of the disclosure comprise one or more peptides of the first aspect of the disclosure complexed with a lipid component where the lipid component comprises sphingomyelin and one or more additional phospholipids. PALM according to the present disclosure may be passively or actively delivered to a target cell population. In one embodiment of the second aspect of the disclosure, PALM comprises one or more peptides of the present disclosure where the lipid component consists essentially of sphingomyelin and one or more additional phospholipids. In one embodiment PALM comprises a peptide of the present disclosure and a lipid component wherein the lipid component comprises sphingomyelin and one or more additional phospholipids where the additional phospholipid is selected from the group consisting of phosphatidylcholine, polyethylene glycol-phosphatidylethanolamine (PEG-PE), phosphatidylethanolamine, phosphatidylglycerol, phosphatidylserine, phosphatidylinositol, cardiolipin, and any combination thereof. In another embodiment the PALM comprises a peptide of the disclosure and the lipid component comprises sphingomyelin, and phosphatidylcholine. In another embodiment the PALM comprises a peptide of the disclosure, sphingomyelin, and 1-palmitoyl-2-oleoyl phosphatidylcholine (POPC). In yet another embodiment the PALM comprises a peptide of the disclosure and the lipid component comprises sphingomyelin, and phosphatidylethanolamine. In yet another embodiment the PALM comprises a peptide of the disclosure, and the lipid component comprises sphingomyelin, and poly(ethylene glycol)phosphatidyl-ethanolamine. In still another embodiment the PALM comprises a peptide of the disclosure and the lipid component comprises sphingomyelin, and phosphatidylserine. In another embodiment the PALM comprises a peptide of the disclosure and the lipid component comprises sphingomyelin and cardiolipin.

In still another embodiment of the second aspect of the disclosure, PALM comprises a peptide of the disclosure and the lipid component consists essentially of sphingomyelin and one or more additional phospholipid where the one or more additional phospholipid is selected from the group consisting of phosphatidylcholine, polyethylene glycol-phosphatidyl-ethanolamine (PEG-PE), phosphatidylethanolamine, phosphatidylglycerol, phosphatidylserine, phosphatidylinositol, cardiolipin, and any combination thereof. In still another embodiment the PALM comprises a peptide of the disclosure and the lipid component consists essentially of sphingomyelin and phosphatidylcholine. In another embodiment the PALM comprises a peptide of the disclosure and the lipid component consists essentially of sphingomyelin and 1-palmitoyl-2-oleoyl-phosphatidylcholine (POPC).

In some embodiments of the second aspect of the disclosure, PALM comprises a peptide of the disclosure and the lipid component consists essentially of sphingomyelin and one or more additional phospholipid where the one or more additional phospholipid is selected from the group consisting of phosphatidylcholine, polyethylene glycol-phosphatidylethanolamine (PEG-PE), phosphatidylethanolamine, phosphatidylglycerol, phosphatidylserine, phosphatidylinositol, cardiolipin, and any combination thereof where the molar ratio of phospholipid to sphingomyelin is from about 95:5 to about 10:90. In another embodiment the molar ratio of phospholipid to sphingomyelin is from about 90:10 to about 20:80. In still another embodiment the molar ratio of phospholipid to sphingomyelin is from about 25:75 to about 35:65. In another embodiment the molar ratio of phospholipid to sphingomyelin is about 30:70. In another embodiment the molar ratio of phospholipid to sphingomyelin is from about 80:20 to about 60:40. In yet another embodiment the molar ratio of phospholipid to sphingomyelin is from about 75:25 to about 65:35. In still another embodiment the molar ratio of phospholipid to sphingomyelin is about 70:30.

The fatty acid constituents of the phospholipids include fatty acids according to the formula: R—COOH, wherein R is a ($C_7$-$C_{21}$) alkyl group or a ($C_7$-$C_{21}$) alkenyl group wherein the alkenyl group can have from one to six double bonds. Examples of suitable fatty acids include, but are not limited to, phytanic acid, linolenic acid, linoleic acid, docosatetraenoic acid, oleic acid, caprylic acid, lauric acid, arachidic acid, myristic acid and palmitic acid. The pair of fatty acids esterified to the glycerol backbone of a particular phospholipid may be identical or each may be a different type of fatty acid.

The molar ratio of the lipid component to peptide is from about 10:1 to about 2:1. In one embodiment the ration is from about 9:1 to about 2:1. In one embodiment the molar ratio of the lipid component to peptide is from about 8:1 to about 2:1. In still another embodiment the molar ratio of the lipid component to peptide is from about 7:1 to about 3:1. In another embodiment the molar ratio of the lipid component to peptide is from about 6:1 to about 4:1.

Complexes of phosphatidylcholine with amphiphilic peptides are known. One method to produce these complexes is by initial co-lyophilization from a common solvent phase followed by rehydration of the dry lyophilizate to form complexes in aqueous suspension.

Particle size is measured by DLS and is expressed as the hydrodynamic mean diameter ("mean diameter"). PALM according to the second aspect of the disclosure are nanometer-sized particles having a mean diameter of 30 nm or less. In one embodiment the mean particle diameter is from about 5 nm to about 30 nm. In yet another embodiment the mean particle diameter is from about 7.5 nm to about 30 nm. In still another embodiment the mean particle diameter is from about 10 nm to about 30 nm. In another embodiment the mean particle diameter is from about 5 nm to about 25 nm. In another embodiment the mean particle diameter is from about 7.5 nm to about 25 nm. In yet another embodiment the mean particle diameter is from about 10 nm to about 25 nm. In another embodiment the mean particle diameter is from about 5 nm to about 20 nm. In another embodiment the mean particle diameter is from about 7.5 nm to about 20 nm. In yet another embodiment the mean particle diameter is from about 10 nm to about 20 nm. In still another embodiment the mean particle diameter is from about 5 nm to about 15 nm. In another embodiment the mean particle diameter is from about 7.5 nm to about 15 nm. In yet another embodiment the mean particle diameter is from about 10 nm to about 15 nm. In still another embodiment the mean particle diameter is from about 7.5 nm to about 10 nm.

A third aspect of the disclosure provides for PALM-cargo molecule compositions which comprise any one of the PALM embodiments of the second aspect of the disclosure and a cargo molecule. Cargo molecules include, but are not limited to, molecules having pharmaceutical or therapeutic properties. Non-limiting examples of cargo molecules include anti-cancer compounds such as all-trans retinoic acid, alcohol esters of all-trans retinoic acid including methyl-, ethyl-, and longer chain fatty alkyl chain alcohol esters of retinoic acid and cholesteryl esters of retinoic acid; retinoic acid amides such as fenretinide; retinol and carboxylic acid esters of retinol including methyl-, ethyl-, and longer chain fatty alkyl chain alcohol esters of retinoic acid;

lipophilic anti-fungal agents such as amphotericin B or nystatin; steroids such as progesterone, testosterone, prednisolone, hydrocortisone, dexamethasone and estradiols; analgesics such as propofol and haloperidol; antipsychotics such as fluphenazine decanoate and aripiprazole; the vitamin D analogs cholecalciferol and ergocalciferol; and the isomers of vitamin E, either collectively or individually.

Cargo molecules also include molecules enabling diagnostic or imaging procedures such as fluorescent imaging agents, radiolabeled imaging agents, and agents used for MRI, PET, CT, SPECT/CT and x-ray studies. MRI imaging agents include, but are not limited to, contrast agents such as a phosphatidylethanolamine with a diethylenetriamine pentaacetic acid moiety that is chelated with a gadolinium ion or similar lanthanide ion or indium-111 or gallium-67 or lutetium-177 or samarium-153.

Cargo molecules may also be various types and lengths of RNA or DNA that have been linked to cholesterol or other polycyclic fatty alcohols by known methods.

In one embodiment of the third aspect, the cargo molecule is miriplatin which has the chemical name: cis-[((1R, 2R)-1,2-cyclohexanediamine-N,N')bis(myristato)] platinum(II).

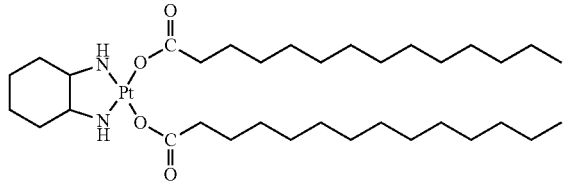

Yet another embodiments of the third aspect of the disclosure, is a PALM-cargo molecule complex wherein the cargo molecule is a compound conjugate of formula I A-R-L-X            (formula I)

wherein A is an agent having an hydroxy or amine group; R is a hydroxyl or an amine group of the agent; L is a linker, and X is an anchor moiety.

Another embodiment of the third aspect of the disclosure is a PALM-cargo molecule complex wherein the cargo molecule is a compound conjugate of formula I:

A-R-L-X            (formula I)

wherein A is an agent having a hydroxy or amine group; R is the hydroxyl or the amine group of the agent; L is carbonic acid, succinic acid or diglycolic acid; and X is cholesterol, α-tocotrienol, β-tocotrienol, γ-tocotrienol, δ-tocotrienol, cholesterol, coprostanol, plant sterols, (ß-sitosterol, sitostanol, stigmasterol, stigmastanol, campesterol, brassicasterol), ergosterol, retinol, cholecalciferol, ergocalciferol, tocopherol, or tocotrienol.

Another embodiment of the third aspect of the disclosure is a PALM-cargo molecule complex wherein the cargo molecule is a compound conjugate of formula I:
wherein A is an agent having a hydroxy or amine group; R is the hydroxyl or the amine group of the agent; L is selected from the group consisting of carbonic acid, succinic acid or diglycolic acid; and X is selected from the group consisting of cholesterol, α-tocotrienol, β-tocotrienol, γ-tocotrienol, δ-tocotrienol, cholesterol, coprostanol, plant sterols, (ß-sitosterol, sitostanol, stigmasterol, stigmastanol, campesterol, brassicasterol), ergosterol, retinol, cholecalciferol, ergocalciferol, α-tocopherol, β-tocopherol, γ-tocopherol, and δ-tocopherol, Another embodiment of the third aspect of the disclosure is a PALM-cargo molecule complex wherein the cargo molecule is a compound conjugate of formula I:

wherein A is an agent having a hydroxy or amine group; R is a hydroxyl or an amine group of the agent; L is a linker; and X is an anchor moiety selected from the group consisting of cholesterol, cholecalciferol and δ-tocotrienol.

In one embodiment of a compound conjugate of formula (1), R is a hydroxy group of the agent, and the anchor moiety is covalently bonded to agent by a carbonate ester bond. In another embodiment of a compound conjugate of formula (1), R is an amine group of the agent, and the anchor moiety is covalently bonded to agent by a carbamate ester bond.

In another embodiment of a compound conjugate of formula (1), the anchor moiety is cholesterol. In still another embodiment of a compound conjugate of formula (1), the anchor moiety is cholesterol, with the proviso that if the anchor moiety is cholesterol, then the compound is not paclitaxel.

In yet another embodiment of a compound conjugate of formula (1) the anchor moiety is α-tocotrienol. In another embodiment of a compound conjugate of formula (1) the anchor moiety is β-tocotrienol. In still another embodiment of a compound conjugate of formula (1) the anchor moiety is γ-tocotrienol. In yet another embodiment of a compound conjugate of formula (1) the anchor moiety is δ-tocotrienol.

In some embodiments of the compound conjugate of formula (1) the agent is a drug.

In some embodiments of the compound conjugate of formula (1) the agent is an anti-cancer drug. In one embodiment of the compound conjugate of formula (1) the agent is an anti-cancer drug and the anti-cancer drug is covalently bonded to the anchor by a carbonate ester bond.

In one embodiment of the compound conjugate of formula (1) the agent is an anti-cancer drug and the anti-cancer drug is covalently bonded to the anchor by a carbamate ester bond.

Non-limiting examples of anti-cancer drugs having a hydroxyl group available to form the carbonate ester bond include AZD2811, a hydroxy camptothecin, doxorubicin, troxacitabine, vincristine, sirolimus, tubulysin A, docetaxel, or paclitaxel Non-limiting examples of anti-cancer drugs having an amine available for forming the carbamate ester bond include, doxorubicin, daunorubicin, gemcitabine, cytarabine and troxacitabine.

In some embodiments of the PALM-cargo molecule compositions of the third aspect of the disclosure, the cargo molecule is paclitaxel 2'-cholesteryl carbonate. In another embodiment the cargo molecule is paclitaxel 2'-δ-tocotrienyl carbonate.

In yet other embodiments, the cargo molecule is docetaxel 2'-cholesteryl carbonate. In other embodiments, the cargo molecule is the cholesteryl carbonate ester of 10-hydroxycamptothecin. In still other embodiments, the cargo molecule is the cholesteryl carbonate ester of 7-ethyl-10-hydroxycamptothecin, which is the active metabolite of irinotecan. In another embodiment, the cargo molecule is the cholesteryl carbonate ester of sirolimus. In other embodiments, the cargo molecule is the cholesteryl carbonate ester of gemcitabine. In other embodiments, the cargo molecule is the cholesteryl carbonate ester of tubulysin A. In other embodiments, the cargo molecule is a cholesteryl carbonate ester of morphine, a cholesteryl carbonate ester of hydromorphone, or a cholesteryl carbonate ester of codeine.

In other embodiments of the PALM-cargo molecule compositions of the third aspect of the disclosure, the cargo molecule is the cholesteryl carbamate ester of gemcitabine (Cholesteryl ($N^4$)-Gemcitabine Carbamate). In yet other embodiments, the cargo molecule is the cholesteryl carbamate ester of adenosine. In yet other embodiments, the cargo molecule is the cholesteryl carbonate ester of doxorubicin, the structure of which is:

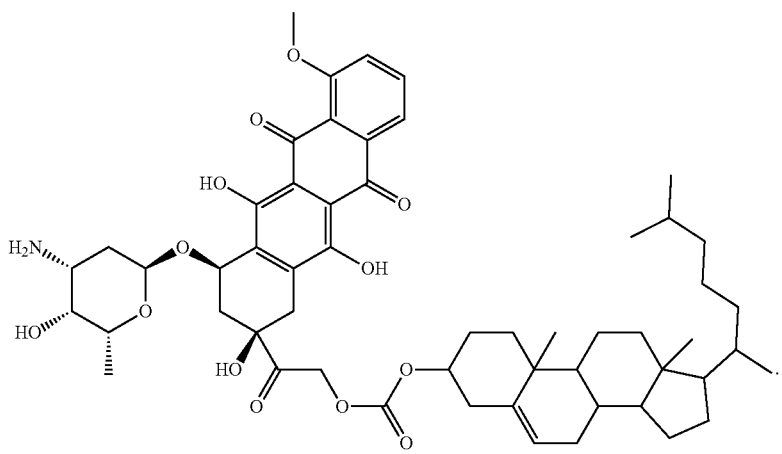 [SMILES: COc1cccc2c1C(=O)c1c(O)c3c(c(O)c1C2=O)C[C@](O)(C(=O)COC(=O)OC1CCC2(C)C(=CCC4C2CCC2(C)C(C(C)CCCC(C)C)CCC42)C1)C[C@H]3O[C@@H]1C[C@@H](N)[C@@H](O)[C@@H](C)O1]
In yet another embodiments, the cargo molecule is the cholesteryl carbonate ester of vincristine, the structure of which is:
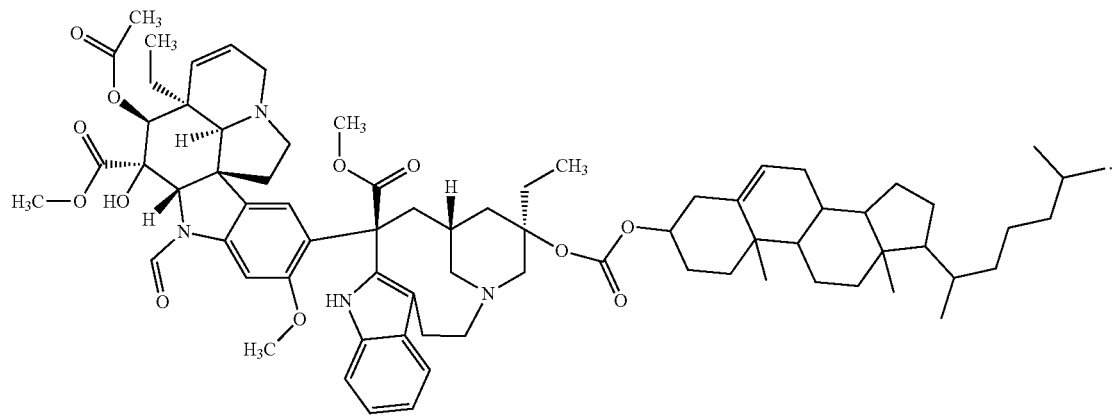
In still another embodiment the cargo molecule is the delta-tocotrienyl carbonate ester of paclitaxel, the structure of which is:
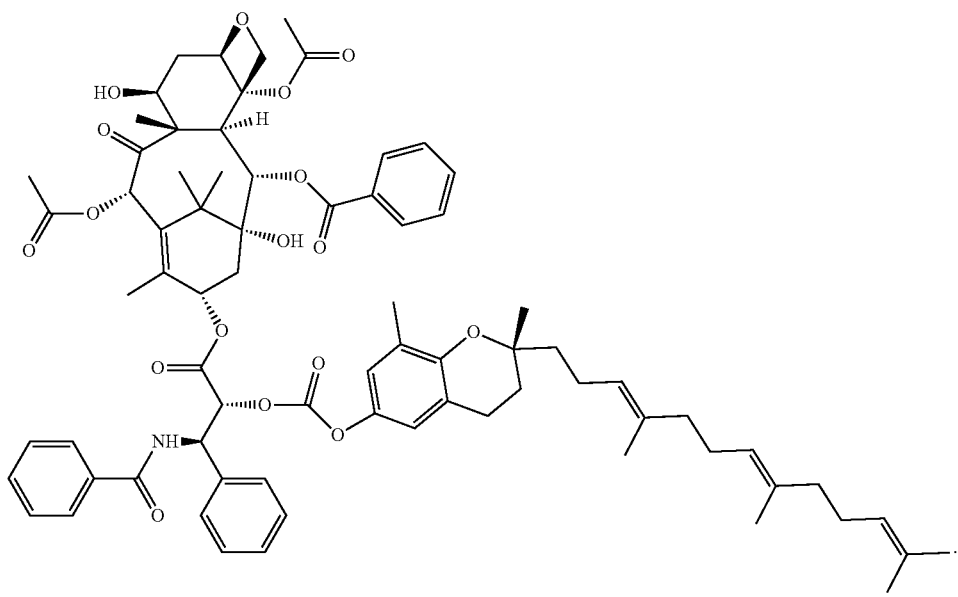 [SMILES: CC(=O)O[C@@H]1C(=O)[C@@]2(C)[C@H]([C@H](OC(=O)c3ccccc3)[C@@]3(O)C[C@H](OC(=O)[C@H](OC(=O)Oc4cc(C)c5c(c4)CC[C@@](C)(CC/C=C(\C)CC/C=C(\C)CCC=C(C)C)O5)[C@H](NC(=O)c4ccccc4)c4ccccc4)C(C)=C1C3(C)C)[C@]1(OC(C)=O)CO[C@@H]1C[C@@H]2O]

In still another embodiment the cargo molecule is the gemcitabine delta-tocotrienlyl carbamate ester, the structure of which is:

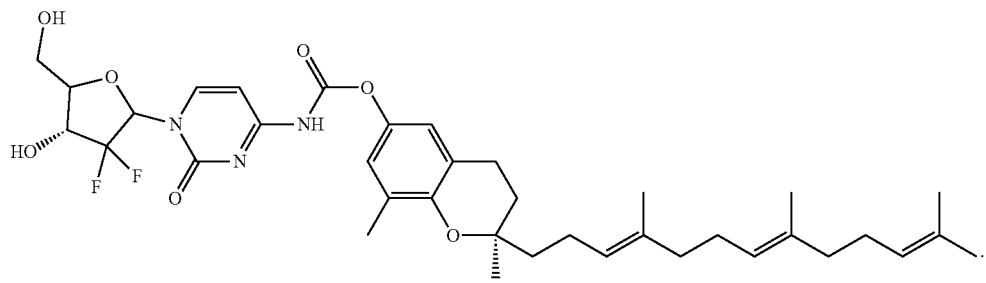 [SMILES: CC(C)=CCC/C(C)=C/CC/C(C)=C/CC[C@]1(C)CCc2cc(OC(=O)Nc3ccn(C4OC(CO)[C@@H](O)C4(F)F)c(=O)n3)cc(C)c2O1]

In yet another embodiment the cargo molecule is the Doxorubicin delta-tocotrienlyl carbonate ester, the structure of which is:

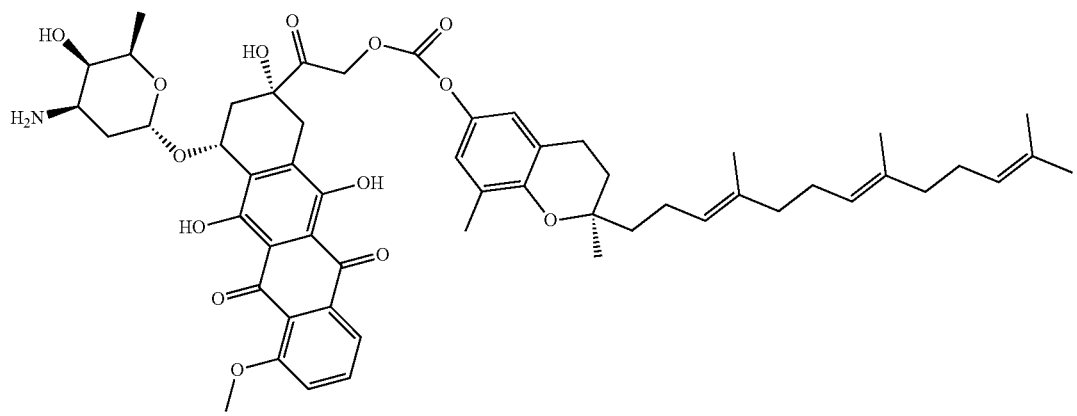 [SMILES: COc1cccc2c1C(=O)c1c(O)c3c(c(O)c1C2=O)C[C@](O)(C(=O)COC(=O)Oc1cc(C)c2c(c1)CC[C@@](C)(CC/C=C(\C)CC/C=C(\C)CCC=C(C)C)O2)C[C@H]3O[C@@H]1C[C@@H](N)[C@@H](O)[C@@H](C)O1]

Table 4 provides the structure of non-limiting examples of agents (A) useful in the present invention with the hydroxyl or amine group (R) indicated by an arrow.

TABLE 4

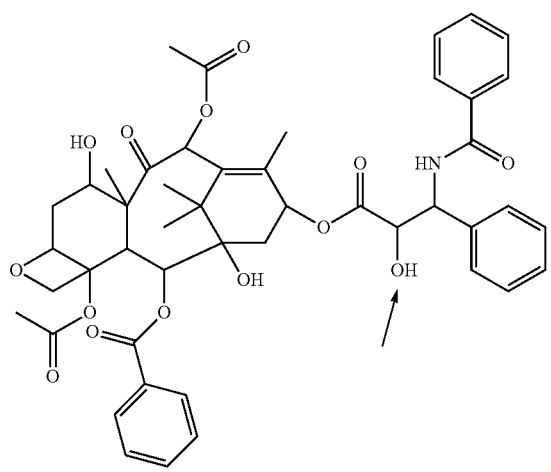 [SMILES: CC(=O)OC1C(=O)C2(C)C(O)CC3OCC3(OC(C)=O)C2C(OC(=O)c2ccccc2)C2(O)CC(OC(=O)C(O)C(NC(=O)c3ccccc3)c3ccccc3)C(C)=C1C2(C)C]

Paclitaxel

TABLE 4-continued
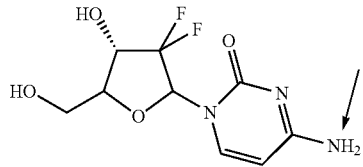 [SMILES: Nc1ccn(C2OC(CO)[C@H](O)C2(F)F)c(=O)n1]
Gemcitabine
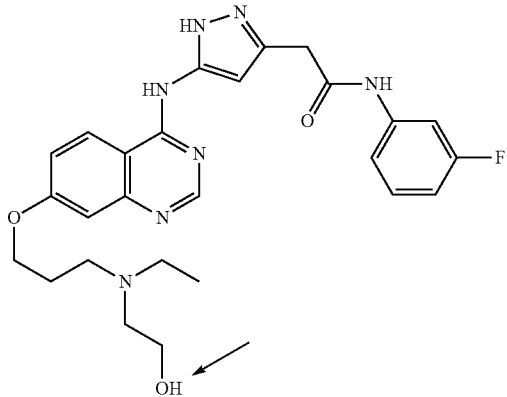 [SMILES: CCN(CCO)CCCOc1ccc2c(Nc3cc(CC(=O)Nc4cccc(F)c4)n[nH]3)ncnc2c1]
AZD2811
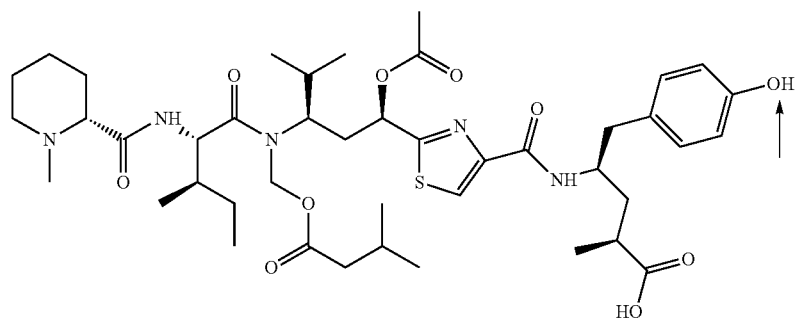 [SMILES: CC[C@@H](C)[C@H](NC(=O)[C@H]1CCCCN1C)C(=O)N(COC(=O)CC(C)C)[C@H](C[C@@H](OC(C)=O)c1nc(C(=O)N[C@@H](Cc2ccc(O)cc2)C[C@H](C)C(=O)O)cs1)C(C)C]
Tubulysin A
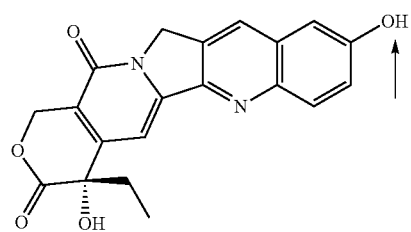 [SMILES: CC[C@@]1(O)C(=O)OCc2c1cc1n(c2=O)Cc2cc3cc(O)ccc3nc2-1]
10-Hydroxy-camptothecin TABLE 4-continued

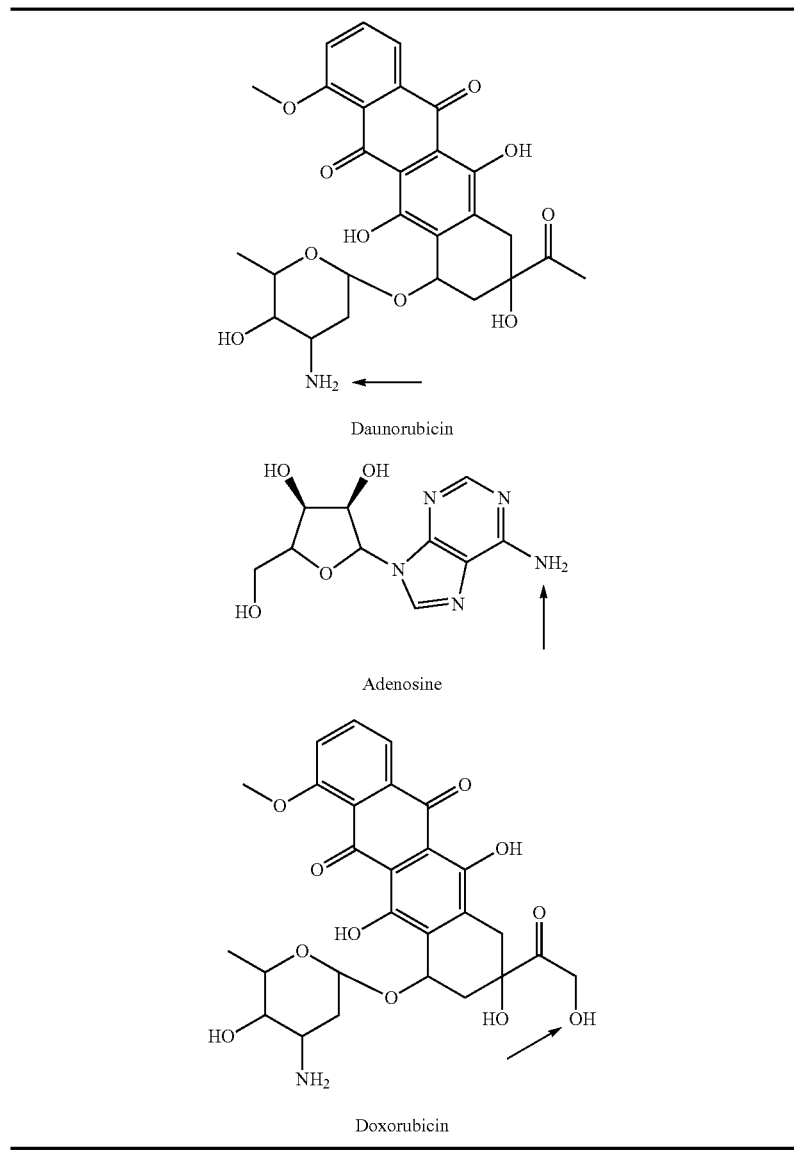

Daunorubicin

Adenosine

Doxorubicin

Table 5 provides non-liming examples of PALM-cargo compositions of formula A-R-L-X.

TABLE 5

| Compound | A | R | L | X |
|---|---|---|---|---|
| 1 | Paclitaxel | OH | Carbonic Acid | γ-Tocotrienol |
| 2 | Paclitaxel | OH | Carbonic Acid | δ-Tocotrienol |
| 3 | Paclitaxel | OH | Carbonic Acid | Cholecalciferol |
| 4 | Paclitaxel | OH | Carbonic Acid | Ergocalciferol |
| 5 | Paclitaxel | OH | Succinic Acid | Cholesterol |
| 6 | Paclitaxel | OH | Succinic Acid | γ-Tocotrienol |
| 7 | Paclitaxel | OH | Succinic Acid | δ-Tocotrienol |
| 8 | Paclitaxel | OH | Succinic Acid | Cholecalciferol |
| 9 | Paclitaxel | OH | Succinic Acid | Ergocalciferol |
| 10 | Paclitaxel | OH | Diglycolic Acid | Cholesterol |
| 11 | Paclitaxel | OH | Diglycolic Acid | γ-Tocotrienol |
| 12 | Paclitaxel | OH | Diglycolic Acid | δ-Tocotrienol |
| 13 | Paclitaxel | OH | Diglycolic Acid | Cholecalciferol |
| 14 | Paclitaxel | OH | Diglycolic Acid | Ergocalciferol |
| 15 | Gemcitabine | $NH_2$ | Carbonic Acid | Cholesterol |
| 16 | Gemcitabine | $NH_2$ | Carbonic Acid | γ-Tocotrienol |
| 17 | Gemcitabine | $NH_2$ | Carbonic Acid | δ-Tocotrienol |

TABLE 5-continued

| Compound | A | R | L | X |
|---|---|---|---|---|
| 18 | Gemcitabine | NH$_2$ | Carbonic Acid | Cholecalciferol |
| 19 | Gemcitabine | NH$_2$ | Carbonic Acid | Ergocalciferol |
| 20 | Gemcitabine | NH$_2$ | Succinic Acid | Cholesterol |
| 21 | Gemcitabine | NH$_2$ | Succinic Acid | γ-Tocotrienol |
| 22 | Gemcitabine | NH$_2$ | Succinic Acid | δ-Tocotrienol |
| 23 | Gemcitabine | NH$_2$ | Succinic Acid | Cholecalciferol |
| 24 | Gemcitabine | NH$_2$ | Succinic Acid | Ergocalciferol |
| 25 | Gemcitabine | NH$_2$ | Diglycolic Acid | Cholesterol |
| 26 | Gemcitabine | NH$_2$ | Diglycolic Acid | γ-Tocotrienol |
| 27 | Gemcitabine | NH$_2$ | Diglycolic Acid | δ-Tocotrienol |
| 28 | Gemcitabine | NH$_2$ | Diglycolic Acid | Cholecalciferol |
| 29 | Gemcitabine | NH$_2$ | Diglycolic Acid | Ergocalciferol |
| 30 | AZD2811 | OH | Carbonic Acid | Cholesterol |
| 31 | AZD2811 | OH | Carbonic Acid | γ-Tocotrienol |
| 32 | AZD2811 | OH | Carbonic Acid | δ-Tocotrienol |
| 33 | AZD2811 | OH | Carbonic Acid | Cholecalciferol |
| 34 | AZD2811 | OH | Carbonic Acid | Ergocalciferol |
| 35 | AZD2811 | OH | Succinic Acid | Cholesterol |
| 36 | AZD2811 | OH | Succinic Acid | γ-Tocotrienol |
| 37 | AZD2811 | OH | Succinic Acid | δ-Tocotrienol |
| 38 | AZD2811 | OH | Succinic Acid | Cholecalciferol |
| 39 | AZD2811 | OH | Succinic Acid | Ergocalciferol |
| 40 | AZD2811 | OH | Diglycolic Acid | Cholesterol |
| 41 | AZD2811 | OH | Diglycolic Acid | γ-Tocotrienol |
| 42 | AZD2811 | OH | Diglycolic Acid | δ-Tocotrienol |
| 43 | AZD2811 | OH | Diglycolic Acid | Cholecalciferol |
| 44 | AZD2811 | OH | Diglycolic Acid | Ergocalciferol |
| 45 | Daunorubicin | NH$_2$ | Carbonic Acid | Cholesterol |
| 46 | Daunorubicin | NH$_2$ | Succinic Acid | γ-Tocotrienol |
| 47 | Daunorubicin | NH$_2$ | Carbonic Acid | δ-Tocotrienol |
| 48 | Daunorubicin | NH$_2$ | Carbonic Acid | Cholecalciferol |
| 49 | Daunorubicin | NH$_2$ | Carbonic Acid | Ergocalciferol |
| 50 | Daunorubicin | NH$_2$ | Succinic Acid | Cholesterol |
| 51 | Daunorubicin | NH$_2$ | Succinic Acid | γ-Tocotrienol |
| 52 | Daunorubicin | NH$_2$ | Succinic Acid | δ-Tocotrienol |
| 53 | Daunorubicin | NH$_2$ | Succinic Acid | Cholecalciferol |
| 54 | Daunorubicin | NH$_2$ | Succinic Acid | Ergocalciferol |
| 55 | Daunorubicin | NH$_2$ | Diglycolic Acid | Cholesterol |
| 56 | Daunorubicin | NH$_2$ | Diglycolic Acid | γ-Tocotrienol |
| 57 | Daunorubicin | NH$_2$ | Diglycolic Acid | δ-Tocotrienol |
| 58 | Daunorubicin | NH$_2$ | Diglycolic Acid | Cholecalciferol |
| 59 | Daunorubicin | NH$_2$ | Diglycolic Acid | Ergocalciferol |
| 60 | 10-Hydroxy-camptothecin | OH | Carbonic Acid | Cholesterol |
| 61 | 10-Hydroxy-camptothecin | OH | Carbonic Acid | γ-Tocotrienol |
| 62 | 10-Hydroxy-camptothecin | OH | Carbonic Acid | δ-Tocotrienol |
| 63 | 10-Hydroxy-camptothecin | OH | Carbonic Acid | Cholecalciferol |
| 64 | 10-Hydroxy-camptothecin | OH | Carbonic Acid | Ergocalciferol |
| 65 | 10-Hydroxy-camptothecin | OH | Succinic Acid | Cholesterol |
| 66 | 10-Hydroxy-camptothecin | OH | Succinic Acid | γ-Tocotrienol |
| 67 | 10-Hydroxy-camptothecin | OH | Succinic Acid | δ-Tocotrienol |
| 68 | 10-Hydroxy-camptothecin | OH | Succinic Acid | Cholecalciferol |
| 69 | 10-Hydroxy-camptothecin | OH | Succinic Acid | Ergocalciferol |
| 70 | 10-Hydroxy-camptothecin | OH | Diglycolic Acid | Cholesterol |
| 71 | 10-Hydroxy-camptothecin | OH | Diglycolic Acid | γ-Tocotrienol |
| 72 | 10-Hydroxy-camptothecin | OH | Diglycolic Acid | δ-Tocotrienol |
| 73 | 10-Hydroxy-camptothecin | OH | Diglycolic Acid | Cholecalciferol |
| 74 | 10-Hydroxy-camptothecin | OH | Diglycolic Acid | Ergocalciferol |
| 75 | Adenosine | NH$_2$ | Carbonic Acid | Cholesterol |
| 76 | Adenosine | NH$_2$ | Carbonic Acid | γ-Tocotrienol |
| 77 | Adenosine | NH$_2$ | Carbonic Acid | δ-Tocotrienol |
| 78 | Adenosine | NH$_2$ | Carbonic Acid | Cholecalciferol |
| 79 | Adenosine | NH$_2$ | Carbonic Acid | Ergocalciferol |
| 80 | Adenosine | NH$_2$ | Succinic Acid | Cholesterol |
| 81 | Adenosine | NH$_2$ | Succinic Acid | γ-Tocotrienol |
| 82 | Adenosine | NH$_2$ | Succinic Acid | δ-Tocotrienol |
| 83 | Adenosine | NH$_2$ | Succinic Acid | Cholecalciferol |
| 84 | Adenosine | NH$_2$ | Succinic Acid | Ergocalciferol |
| 85 | Adenosine | NH$_2$ | Diglycolic Acid | Cholesterol |
| 86 | Adenosine | NH$_2$ | Diglycolic Acid | γ-Tocotrienol |
| 87 | Adenosine | NH$_2$ | Diglycolic Acid | δ-Tocotrienol |
| 88 | Adenosine | NH$_2$ | Diglycolic Acid | Cholecalciferol |
| 89 | Adenosine | NH$_2$ | Diglycolic Acid | Ergocalciferol |
| 90 | Tubulysin A | OH | Carbonic Acid | Cholesterol |
| 91 | Tubulysin A | OH | Carbonic Acid | γ-Tocotrienol |
| 92 | Tubulysin A | OH | Carbonic Acid | δ-Tocotrienol |
| 93 | Tubulysin A | OH | Carbonic Acid | Cholecalciferol |
| 94 | Tubulysin A | OH | Carbonic Acid | Ergocalciferol |
| 95 | Tubulysin A | OH | Succinic Acid | Cholesterol |

TABLE 5-continued

| Compound | A | R | L | X |
|---|---|---|---|---|
| 96 | Tubulysin A | OH | Succinic Acid | γ-Tocotrienol |
| 97 | Tubulysin A | OH | Succinic Acid | δ-Tocotrienol |
| 98 | Tubulysin A | OH | Succinic Acid | Cholecalciferol |
| 99 | Tubulysin A | OH | Succinic Acid | Ergocalciferol |
| 100 | Tubulysin A | OH | Diglycolic Acid | Cholesterol |
| 101 | Tubulysin A | OH | Diglycolic Acid | γ-Tocotrienol |
| 102 | Tubulysin A | OH | Diglycolic Acid | δ-Tocotrienol |
| 103 | Tubulysin A | OH | Diglycolic Acid | Cholecalciferol |
| 104 | Tubulysin A | OH | Diglycolic Acid | Ergocalciferol |
| 105 | Doxorubicin | OH | Carbonic Acid | Cholesterol |
| 106 | Doxorubicin | OH | Carbonic Acid | γ-Tocotrienol |
| 107 | Doxorubicin | OH | Carbonic Acid | δ-Tocotrienol |
| 108 | Doxorubicin | OH | Carbonic Acid | Cholecalciferol |
| 109 | Doxorubicin | OH | Carbonic Acid | Ergocalciferol |
| 110 | Doxorubicin | OH | Succinic Acid | Cholesterol |
| 111 | Doxorubicin | OH | Succinic Acid | γ-Tocotrienol |
| 112 | Doxorubicin | OH | Succinic Acid | δ-Tocotrienol |
| 113 | Doxorubicin | OH | Succinic Acid | Cholecalciferol |
| 114 | Doxorubicin | OH | Succinic Acid | Ergocalciferol |
| 115 | Doxorubicin | OH | Diglycolic Acid | Cholesterol |
| 116 | Doxorubicin | OH | Diglycolic Acid | γ-Tocotrienol |
| 117 | Doxorubicin | OH | Diglycolic Acid | δ-Tocotrienol |
| 118 | Doxorubicin | OH | Diglycolic Acid | Cholecalciferol |
| 119 | Doxorubicin | OH | Diglycolic Acid | Ergocalciferol |

A fourth aspect of the disclosure provides for a surprisingly effective co-lyophilization techniques to produce PALM or PALM-cargo molecule compositions from a homogenous solvent phase composed of tert-butyl alcohol and water. The advantages of this approach are: 1) all PALM constituents including peptide, phosphopholipid and optional lipophilic cargo (e.g. paclitaxel-2'-cholesteryl carbonate), are co-solubilized in a single solvent phase, 2) the solvent components are totally miscible and well-suited to removal by standard lyophilization procedure, 3) the procedures avoids potentially toxic substances because tert-butyl alcohol is a low toxicity, class 3 solvent and 4) the resultant dried lyophilizate enables opportunities for greater stability during storage than is possible with aqueous preparations.

The solvent mixture used to prepare PALM is preferably a mixture of tert-butyl alcohol (TBA) and water. In one embodiment the percent ration of TBA to water is between about 70%:30% to about 90%: 10%. In another embodiment the ratio is between about 75%:25% and about 85%: 15%. In yet another embodiment the ratio is 80%:20%.

One embodiment of the fourth aspect provides a process for preparing PALM comprises the steps:

i) solubilizing an amphiphilic peptide in a first solvent mixture to provide a peptide solution;

ii) solubilizing a sphingomyelin in a second solvent mixture to provide a sphingomyelin solution iii) solubilizing an additional phospholipid in a third solvent mixture to provide a phospholipid solution;

iv) combining the peptide solution, the sphingomyelin solution and the phospholipid solution to form a peptide/sphingomyelin/phospholipid solution; and v) lyophilizing the peptide/sphingomyelin/phospholipid solution, wherein steps i), ii), and iii) are performed in any order; and wherein the first, second, and third solvent mixture comprises tert-butyl alcohol and water.

Another embodiment of the fourth aspect of the disclosure provides a process for preparing PALM comprises the steps:

i) combining an amphiphilic peptide, sphingomyelin and an additional phospholipid, to form a peptide/sphingomyelin/phospholipid mixture;

ii) solubilizing the peptide/sphingomyelin/phospholipid mixture in a solvent mixture to form a peptide sphingomyelin/phospholipid solution; and iii) lyophilizing the peptide/phospholipid solution, wherein the solvent mixture comprises tert-butyl alcohol and water.

The forth aspect of the present disclosure additionally provides a process for preparing PALM comprising a cargo molecule to form a PALM-cargo molecule complex. To prepare a PALM-cargo molecule complex, the peptide, sphingomyelin, one or more additional phospholipid and a cargo molecule are each separately prepared in a solvent mixture and, depending on the desired formulation, are combined in specific molar ratios. Alternately, the peptide, sphingomyelin, one or more additional phospholipid and a cargo molecule can be combined directly, without prior solubilization, and then brought into solution with the desired solvent mixture prior to lyophilization.

One embodiment of the fourth aspect of the disclosure provides a process for preparing a PALM-cargo molecule complex comprising the steps:

i) solubilizing an amphiphilic peptide in a first solvent mixture to provide a peptide solution;

ii) solubilizing a sphingomyelin in a second solvent mixture to provide a sphingomyelin solution iii) solubilizing an additional phospholipid in a third solvent mixture to provide a phospholipid solution;

iv) solubilizing a cargo molecule in a fourth solvent mixture to provide a cargo molecule solution;

v) combining the peptide solution, the sphingomyelin solution, the phospholipid solution and the cargo molecule solution to form a peptide/sphingomyelin/phospholipid/cargo molecule solution; and vi) lyophilizing the peptide/sphingomyelin/phospholipid/cargo molecule solution, wherein steps i) ii), iii) and iv) are performed in any order; and wherein the first, second, third and fourth solvent mixture comprise tert-butyl alcohol and water.

Another embodiment of preparing a PALM-cargo molecule complex comprises the steps:

i) combining an amphiphilic peptide, sphingomyelin, an additional phospholipid and a cargo molecule, to form a peptide/sphingomyelin/phospholipid/cargo molecule mixture;

ii) solubilizing the peptide/sphingomyelin/phospholipid/cargo molecule mixture in a solvent mixture to form a peptide/phospholipid solution; and iii) lyophilizing the peptide/sphingomyelin/phospholipid/cargo molecule solution, wherein the solvent mixture comprises tert-butyl alcohol and water The resultant lyophilized cake can be stored for long periods of time and will remain stable. The lyophilized product is rehydrated by adding any suitable aqueous solution, e.g., water or saline, followed by gentle swirling of the contents. Reconstitution of PALM lyophilizates can be enhanced by incubation of the PALM solution at 50° C. for from 5 to 30 minutes. The solution is then filter sterilized (0.2 µm) and stored at 4° C. Alternately, the solvent mixture comprising the peptide, phospholipid and the cargo molecule is filter sterilized prior to lyophilization.

A fifth aspect of the present disclosure provides methods for treating a disorder comprising administering to a subject in need thereof, an effective amount of a PALM-cargo composition according to any one the embodiments of the third aspect of the disclosure.

Scavenger receptor B-1 (SR-B1) is a membrane receptor that binds apolipoprotein A-I, the principle protein component of HDL, to facilitate cellular transport of cholesterol. Cholesterol is an essential nutrient for proliferating cells like those found in malignant tumors. SR-B1 is highly expressed in many tumor cells, including but not limited to breast, prostate, colorectal, pancreatic, adrenal, skin, nasopharyngeal and ovarian cancers. Some amphiphilic peptides are also recognized and bound by SR-BI. PALM are formed from combinations of phospholipid and amphiphilic peptides designed to bind to SR-BI and thereby to selectively deliver cargo molecules to SR-BI-positive cells.

Accordingly one embodiment of the fifth aspect of the present disclosure provides for methods of treating disorders associated with the overexpression of SR-B1 receptors comprising administering a PALM-drug to a subject in need thereof. In one embodiment the method is a method of treating cancer by administering a PALM-cargo molecule composition to a subject in need thereof.

For pharmaceutical use, lyophilized PALM may be provided in single dose or multiple dose containers that can be conveniently reconstituted at the point of use, e.g., hospital or doctor's office using standard diluents such as sterile water for injection, normal sterile saline or sterile 5% dextrose solution. Suitable containers are then aseptically filled with the sterilized mixture, lyophilized and sealed appropriately to maintain sterility of the lyophilized material. Suitable containers include but are not limited to a vial comprising a rubber seal, or the equivalent, that allows for introduction of a diluent for reconstitution, e.g., via a syringe. Such PALM preparations are suitable for parenteral administration including intravenous, subcutaneous, intramuscular, intraperitoneal injection.

EXAMPLES

Example 1

Peptide Synthesis and Purification

Peptides were produced by standard Fmoc solid-phase synthesis techniques at GenScript USA, Inc. (Piscataway, N.J.). Certain peptides were modified at the terminal amino acids by acetylation of the N-terminus and amidation of the C-terminus by standard procedures. Peptides were chromatographically purified to greater than 90% purity by a standard high-performance liquid chromatography method for peptide purification. Purity was confirmed by HPLC and mass spectroscopic analysis.

Example 2

Paclitaxel 2'-Cholesteryl Carbonate (XC) Synthesis

Fifty milligrams of paclitaxel was dissolved in 2 ml of chloroform and then combined with 1.5 molar excess of cholesterol chloroformate in 2 ml of chloroform plus 4 ml of N,N-diisopropylethylamine and 2 ml acetonitrile. The mixture was stirred overnight at ambient temperature and then dried on a rotary evaporator. The resulting off-white precipitate was then dissolved in ethyl acetate/hexane (3:1) and extracted with water, dried, and then redissolved in chloroform. The formation of the product was confirmed by thin-layer chromatography using ethyl acetate/hexane (3:1) as the mobile phase (Rf of paclitaxel 0.4, Rf of Tax-Chol 0.92). Further purification of the product was then carried out on a silica gel column using ethyl acetate/hexane (3:1) as the mobile phase to yield the titled compound (1). The structure was confirmed by mass spectrometry and NMR analysis.

(1)

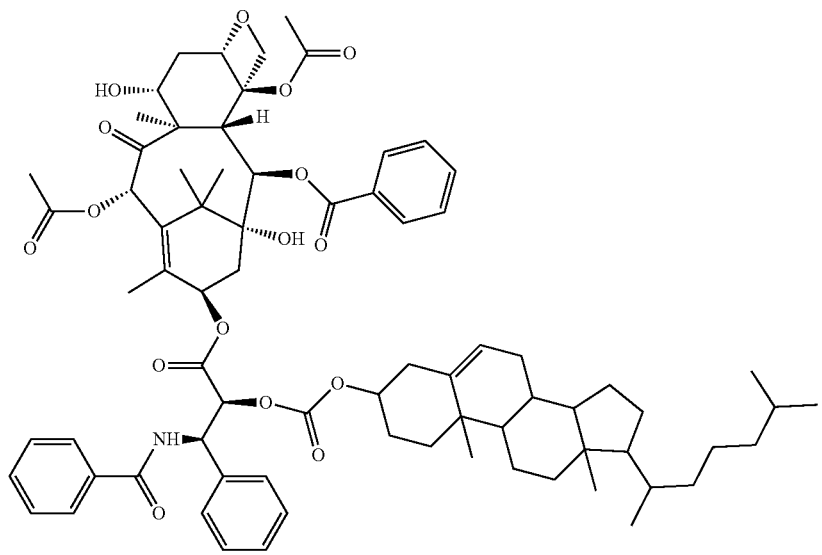

Example 3

Paclitaxel 2'-6-Tocotrienyl Carbonate (XT3) Synthesis
Step 1. Synthesis of p-nitrophenyl carbonate of delta-tocotrienol

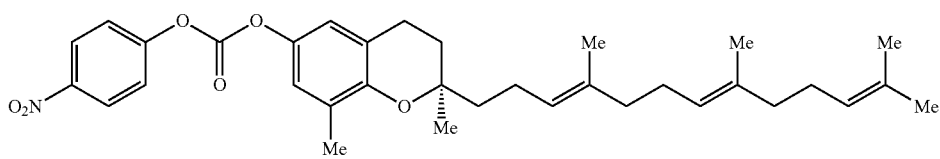

(2)

To the solution of delta-tocotrienol (25 Mg, 0.0629 mmol) in anhydrous methylene chloride (1.5 mL), was added 4-nitrophenyl chloroformate (51 Mg, 0.25 mmol) and tri-ethylmine (35 µL, 0.25 mmol) at room temperature. The reaction mixture was stirred at room temperature for 24 h and then concentrated and then the desired product (2) was obtained using preparative TLC using ethyl acetate/heptanes (10:90) as eluent. The desired product was obtained as yellow powder (18 Mg). $^1$H NMR (CDCl$_3$): δ 8.30 (d, 2H), 7.45 (d, 2H), 6.80 (dd, 2H), 5.05-5.20 (m, 3H), 2.72-2.78 (t, 2H), 2.18 (s, 4H), 1.95-2.15 (m, 4H), 1.72-1.85 (m, 4H), 1.68 (s, 3H), 1.55-1.62 (br s, 12H), 1.30 (br s, 5H).

Step 2. Synthesis of Delta-Tocotrienol Carbonate of Paclitaxel (3)

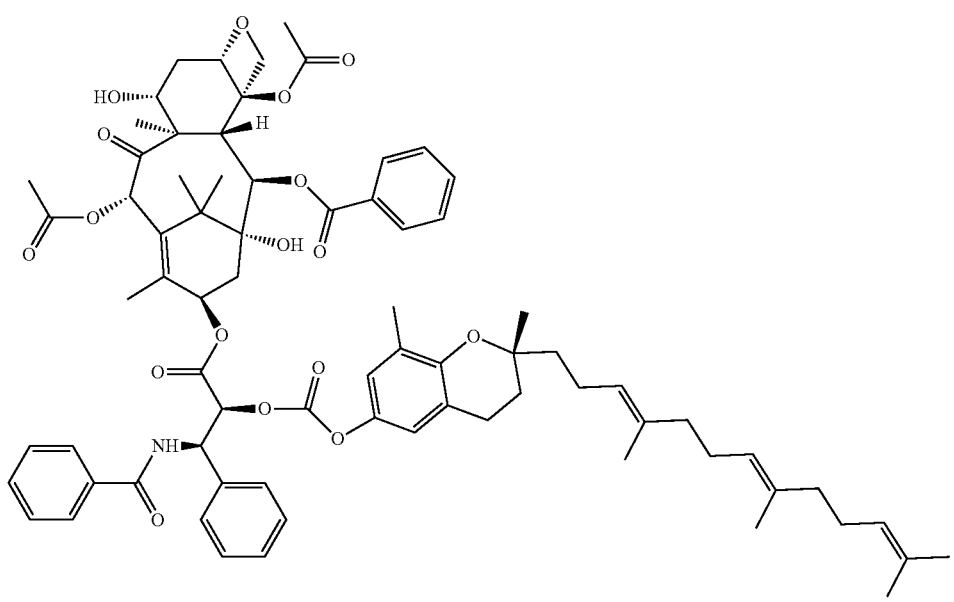

(3)

A solution of compound (2) (18 mg, step 1 product) in methylene chloride (2 mL), paclitaxel (28 mg) and DMAP (10 Mg) are combined at room temperature. The mixture was stirred at room temperature for 24 h. The mixture was concentrated and purified by using preparative TLC using ethyl acetate/heptanes (50:50) as eluent. The desired product (3) (17 Mg) was obtained as colorless solid. TLC Analysis (Rf 0.25, EA/Hexanes: 1:1). $^1$H NMR (CDCl$_3$): δ 8.20 (d, 2H), 7.75 (d, 2H), 7.60-7.62 (m, 1H), 7.30-7.52 (m, 9H), 6.90-6.95 (d, 1H), 6.60-6.75 (dd, 2H), 6.20-6.30 (m, 2H), 6.00-6.05 (m, 1H), 5.70-5.75 (d, 1H), 5.50 (s, 1H), 5.10-5.20 (br s, 2H), 4.95-5.00 (d, 1H), 4.30-4.35 (br s, 1H), 4.20-4.30 (dd, 2H), 3.75-3.80 (d, 1H), 2.70-2.75 (m, 2H), 2.30-2.60 (m, 7H), 2.23-2.27 (m, 11H), 1.50-2.20 (m, 26H), 1.25 (m, 9H), 1.15 (s, 3H)

Example 4

Peptide Amphiphile Lipid Micelle (PALM) Preparation

Separate stock solutions of peptide and phospholipids were prepared in a solvent mixture composed of 80% tert-butyl alcohol (TBA) and 20% water to obtain separate solutions of 10 mM peptide, 20 mM 1,2-dioleoyl-sn-glycero-3-phosphocholine (DOPC) or 20 mM 1-palmitoyl-2-oleoyl-phosphatidylcholine (POPC) and 20 mM egg SM. Aliquots of stock solution were combined to obtain a final solution containing 10 mole equivalents of peptide, 42 mole equivalents of phosphatidylcholine and 18 mole equivalents of SM. The solutions were combined in a 1.5 ml glass vial, frozen (−70° C.), and lyophilized at −5 to −10° C. overnight. The resultant lyophilized cakes were rehydrated by addition of Dulbeco's phosphate buffered saline followed by gentle swirling of the contents. Formation of PALM was completed by incubating the PALM solution at 50° C. for 10 minutes. Some peptide complexes remained turbid upon heating and were also subjected to one cycle of freezing to −80° C. followed by thawing to room temperature in an attempt to obtain a clear solution. The qualities of the PALM preparations were evident in their appearance. A visually clear preparation indicated any nanoparticles that had formed were less than approximately 20 nm diameter. Results are shown in Table 5.

TABLE 5

Stability of Peptide/Phospholipid Complexes by Visual Inspection

| Phospholipid Content[a] | Mole Ratio PC/SM | Mole Ratio $C_{16}$PTX/PL | SEQ ID No. 25[b] | SEQ ID No. 26 | SEQ ID No. 27 | SEQ ID No. 32 |
|---|---|---|---|---|---|---|
| POPC, SM | 70/30 | 0 | Clear | Clear | Clear | Clear |
| POPC, SM | 70/30 | 0.1 | Clear | Turbid | Turbid | Turbid |
| DOPC, SM | 70/30 | 0 | Clear | | Turbid | Turbid |
| DOPC, SM | 70/30 | 0.1 | Clear | | | Turbid |

[a]1-palmitoyl-2-oleoyl phosphatidylcholine (POPC), 1,2-dioleoyl phosphatidylcholine (DOPC), egg sphingomyelin (SM), phosphatidylcholine (PC), phospholipids (PL), paclitaxel 2'-palmitate ($C_{16}$PTX)
[b]Mole ratio of peptide to phospholipids was ¼.

Example 5

Preparation of PALM Containing the Fluorescent Dye DiI

A 40 μl aliquot of 10 mM or peptide was combined with 56 μl of 20 mM POPC, 24 μl 20 mM SM(egg) and 16 μl 2.5 mM DiI in a small glass vial. The peptide and lipid solutions were prepared in 80% TBA/20% water. The DiI stock was prepared in 92% TBA/8% water. The solution was lyophilized and the resultant cake was rehydrated by addition of 0.2 ml of Dulbeco's phosphate buffered saline. The solution was briefly swirled, water bath sonicated (for approx. 15 sec.) and placed in a 50° C. heating block for 20 minutes.

Example 6

Preparation of PALM Containing Miraplatin

A 50 μl aliquot of 10 mM SEQ ID NO:25 in 80% TBA/20% water corresponding to 2.5 mole equivalents of peptide was combined with 3 mole equivalents of POPC and 7 mole equivalents of egg SM from 40 mM and 20 mM stock solutions, respectively, made up of the same solvent mixture. To this was added 0.75 mole equivalents of miriplatin (MedKoo Biosciences, Raleigh, N.C.) from a 1 mM stock solution prepared with 100% TBA. The solution was lyophilized and the resultant cake was rehydrated by addition of 0.4 ml of 5% dextrose in water. The solution was briefly swirled, water bath sonicated (for approx. 15 sec.) and placed in a 50° C. heating block for 20 minutes. The resultant clear solution was passed through a 0.2 μm pore size, polyethersulfone, sterilization filter and stored at 4° C. Particle size analysis (Example 11) by DLS indicated a hydrodynamic mean diameter of 8 nm. SEC confirmed a single particle population comparable to HDL in size. The SEC chromatogram is shown in FIG. 2 (miriplatin (solid line), human HDL (dashed line)).

Example 7

Preparation of PALM Containing Paclitaxel Cholesteryl Carbonate (XC)

Figure 3:
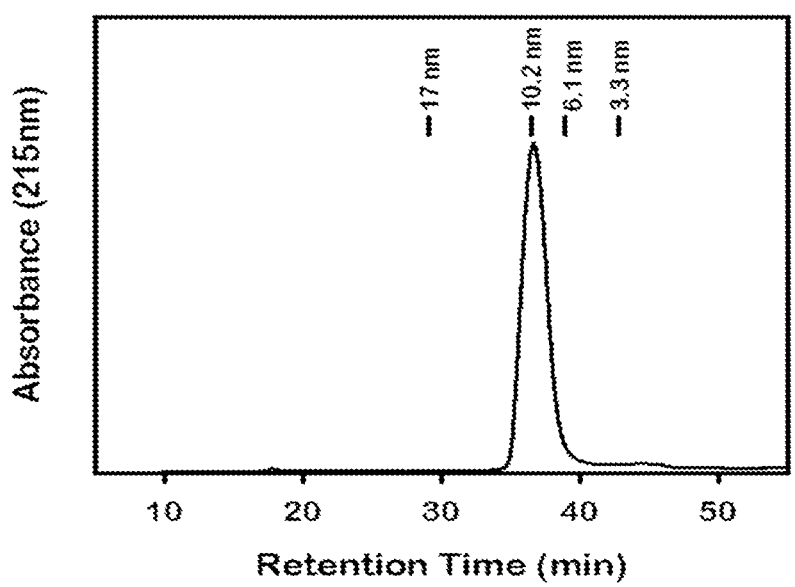
FIG. 3. Shows the size exclusion chromatograph of PALM containing XC and prepared with the peptide of SEQ ID NO:25 at a peptide:phospholipid:XC mole ratio of 1:4:0.4. The elution positions of protein standards of various Stokes diameters are marked.

The preparation of PALM containing XC was essentially as described in Example 6 with the following exceptions. A total of 1.5 mole equivalents of XC from a 10 mM stock solution in 92% TBA/8% water were combined with the other PALM components. The solution was lyophilized and the resultant cake was rehydrated with 0.4 ml of Dulbeco's phosphate buffered saline. The hydrodynamic mean diameter of this preparation, determined by DLS, was 9 nm (Example 11). Size analysis by SEC indicated a single particle population principally 10 nm in diameter (FIG. 3).

Example 8

Preparation of PALM Containing Paclitaxel δ-Tocotrienyl Carbonate (XT3)

A 50 μl aliquot of 10 mM of the peptide of SEQ ID NO:25 in 80% TBA/20% water corresponding to 2.5 mole equivalents of peptide was combined with 7 mole equivalents of POPC and 3 mole equivalents of egg SM from 20 mM stock solutions, made up of the same solvent mixture. To this was added 1 mole equivalent of XT3 from a 10 mM stock solution in 92% TBA/8% water. The lyophilized cake was rehydrated with 0.4 ml of Dulbeco's phosphate buffered saline.

Example 9

R4F is Unsuitable for Preparation of PALM Containing Paclitaxel δ-Tocotrienyl Carbonate (XT3)

Figure 4:
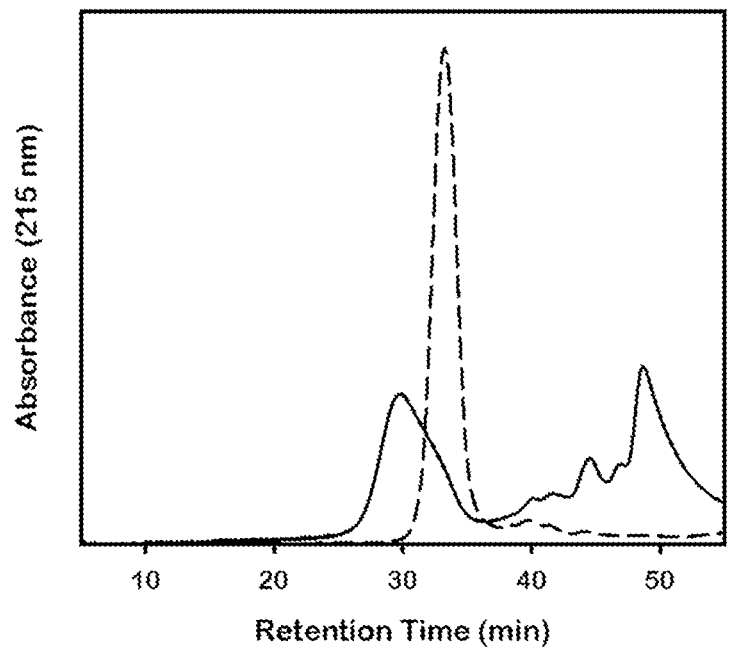
FIG. 4. Comparison of the size exclusion chromatograms for PALM containing XT3 and prepared with peptide of SEQ ID NO:25 (dashed line) or with R4F peptide (solid line). The composition of both was peptide:POPC:SM:XT3 at a mole equivalent ratio of 1:2.8:1.2:0.4.

PALM preparation was conducted as in Example 9 with SEQ ID NO:25 and with R4F (Table 1). Unlike PALM made with the peptide of SEQ ID NO:25, which remained a clear solution at room temperature and 4° C., PALM containing R4F was a clear solution at room temperature but became a hazy gel at 4° C. The gel returned to clear liquid upon warming to room temperature. The PALM preparations were analyzed for size (Example 11). Dynamic light scattering indicated the PALM with the peptide of SEQ ID NO:25 had a mean hydrodynamic diameter of 8 nm (volume intensity). The same analysis for PALM with R4F showed 94% of particle population at a mean hydrodynamic diameter of 11 nm with the remainder at 32 nm. SEC confirmed the uniform size distribution of the PALM with the peptide of SEQ ID NO:25 (FIG. 4). In contrast, the PALM with R4F showed a range of peaks eluting at sizes larger than the SEQ ID NO:25 PALM to sizes smaller than 8 nm. The lack of smaller particle detection by DLS is not surprising since sensitivity for particles below 7 nm is quite weak. These results indicate R4F is not a suitable peptide for PALM preparation.

Example 10

Fenretinide is Loaded in PALM Prepared with the peptide of SEQ ID NO:25

Figure 5:
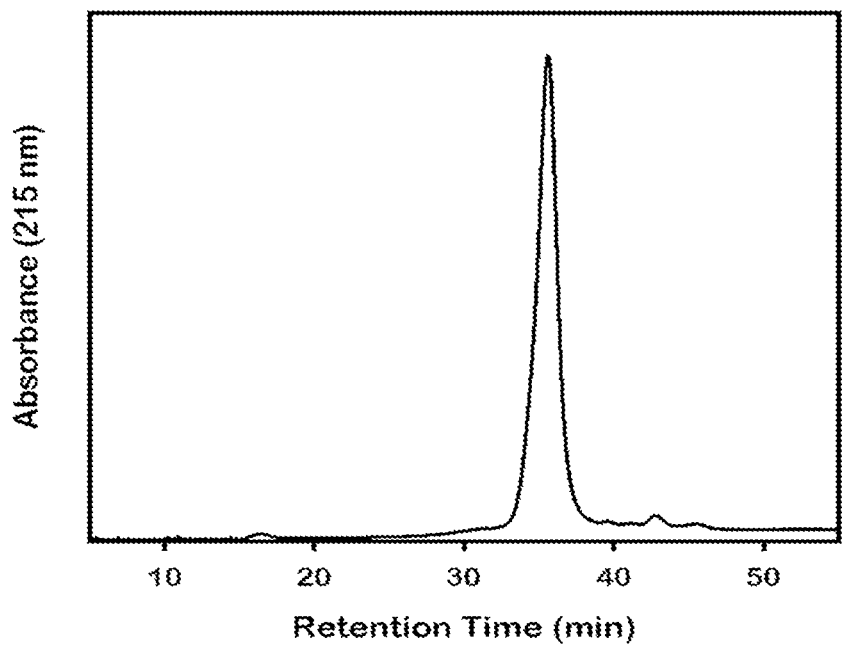
FIG. 5. Depicts the size exclusion chromatogram of PALM prepared with the peptide of SEQ ID NO:25 and containing fenretinide. The PALM composition was peptide:POPC:SM:fenretinide at a mole equivalent ratio of 2.5:3:7:2.

A 35 μl aliquot of 10 mM the peptide of SEQ ID NO:25 in 80% TBA/20% water corresponding to 2.5 mole equivalents of peptide was combined with 3 mole equivalents of POPC and 7 mole equivalents of egg SM from 40 mM and 20 mM stock solutions, respectively, made up in the same solvent mixture. Two mole equivalents of 20 mM fenretinide, in the same solvent mixture, were also added. The solution was lyophilized and the resultant cake was rehydrated with 0.325 ml phosphate buffered saline. The solution became clear within 20 min at 50° C. Analysis by SEC (Example 11) indicated all components eluted as a single peak in the 8 nm-10 nm diameter range (FIG. 5).

Example 11

Determination of PALM Size

The size and size uniformity of the PALM preparations was determined by DLS and SEC. Sizes based on hydrodynamic mean diameters were determined by DLS with a Nicomp 370 particle size analyzer. The analyzer was calibrated with latex standards. Particle sizes referred to herein and in the claims are calculated by DLS as described above unless clearly indicated otherwise.

The relative hydrodynamic size of PALM particles was also determined by SEC with a GE Superose 6 Increase column, (10×300 mm) connected to a Beckman/Coulter Model 126 pump and a Model 128 diode array detector. The mobile phase (150 mM NaCl, 6 mM NaPO4 (pH 7.4)) flow rate was 0.5 ml/min. The eluent was monitored at 215 and 280 nm wavelengths. System performance was confirmed by injection of protein molecular weight standards (FIG. 3).

Example 12

SR-BI Selectivity of PALM in BHK(SR-BI) Cells

Figure 9:
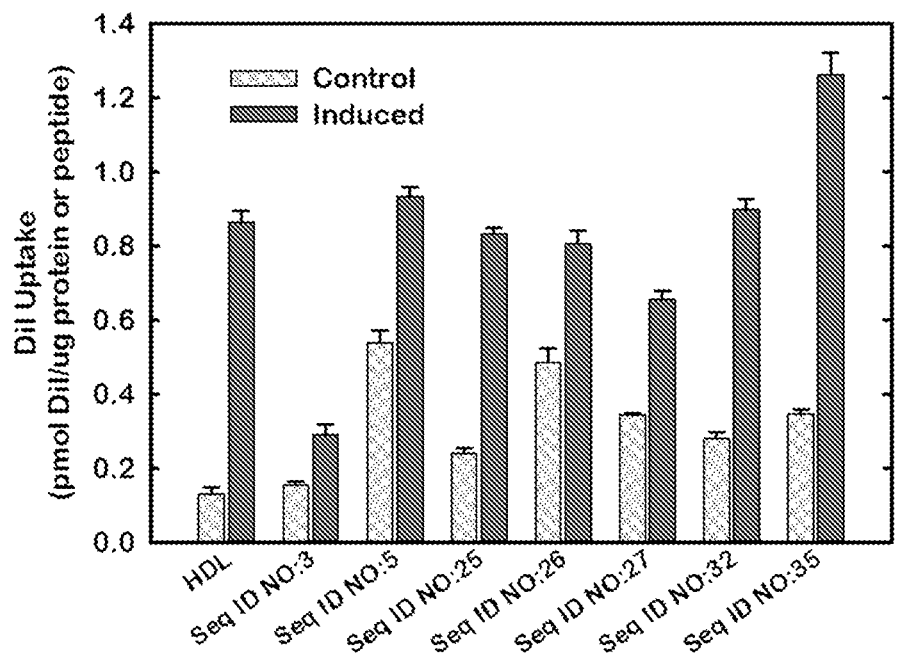
FIG. 9. PALM prepared with various peptides, as indicated, and containing DiI, were incubated with BHK(SR-BI) cells that were stably transfected with a mifepristone inducible, human SR-BI gene. The incubations were performed with un-induced (Control) or induced cells. Human HDL, labeled with DiI, was tested for comparison. The amount of DiI taken up by cells over 4 hours of incubation was detected by fluorescence.

SR-BI interaction studies are done with BHK(SR-BI) cells obtained from the NIH. The cells were stably transfected with an inducible human SR-BI gene by means of the GeneSwitch™ System (Invitrogen). The cells were plated (96-well plate) (8000 cells/well) in growth medium (Dulbeco's modified Eagle medium containing 10% fetal bovine serum) containing 200 ug/ml each of zeocin and hygromycin. After 24 hours incubation, the growth medium was removed and replaced with 0.2% bovine serum albumin in Dulbeco's modified Eagle medium. The medium of cells to be induced for SR-BI expression also contained 10 nM mifepristone, added from a DMSO stock solution. DMSO alone was added to the medium of uninduced cells. The induction medium was removed after 24 hours and replaced with medium containing DiI-labeled PALM (32 µg peptide/ml) or DiI-labeled HDL (19 µg protein/ml) (Kalen Biomedical, Montgomery Village, Md.). The test media were prepared by diluting an aliquot of Di-I-labeled PALM (Example 5) or the DiI-labeled HDL in 0.2% bovine serum albumin in Dulbeco's modified Eagle medium. The solutions were passed through 0.2 µm pore size, polyethersulfone, sterilization filters before use. The cells were incubated for 4 hours. Next, the cells were washed 3 times with 0.1% albumin in Dulbeco's phosphate buffered saline (with calcium and magnesium). The last wash was replaced with 200 ul/well of t-butanol/water (95%/5%). The covered plate was left to stand at ROOM TEMPERATURE for 30 min with occasional shaking. The fluorescence in each well was detected at 520 nm excitation and 580 nm emission with a 550 nm cutoff filter on a Molecular Dynamics Gemini fluorescence plate reader (FIG. 9).

TABLE 6

DiI Uptake from HDL and from PALM Prepared with Various Peptides by BHK(SR-BI) Cells Depends on SR-BI Expression

|  | Un-induced DiI Uptake[a] (pmol/ug/ml) | Induced DiI Uptake (pmol/ug/ml) | Increase Over Un-induced |
|---|---|---|---|
| HDL[b] | 0.13 ± 0.02 | 0.86 ± 0.03 | 561% |
| SEQ ID NO: 3 | 0.16 ± 0.01 | 0.29 ± 0.03 | 88% |
| SEQ ID NO: 5 | 0.54 ± 0.03 | 0.93 ± 0.03 | 73% |
| SEQ ID NO: 25 | 0.24 ± 0.01 | 0.83 ± 0.02 | 245% |
| SEQ ID NO: 26 | 0.49 ± 0.04 | 0.81 ± 0.04 | 65% |
| SEQ ID NO: 27 | 0.34 ± 0.01 | 0.66 ± 0.02 | 90% |
| SEQ ID NO: 32 | 0.28 ± 0.02 | 0.90 ± 0.03 | 221% |
| SEQ ID NO: 35 | 0.35 ± 0.01 | 1.26 ± 0.06 | 264% |

[a]Amount of DiI taken up by cells relative to protein (HDL) or peptide (PALM) concentration. The average (n = 4) and standard error of the mean are shown.
[b]HDL DiI content was 21 pmol/ug protein. PALM DiI content was 40 pmol/ug peptide. HDL concentration was 19 µg/ml. PALM peptide concentrations were 32 µg/ml.

Example 13

Quantification of Paclitaxel

Paclitaxel, XT3 and XC are extracted from aqueous samples by mixing 1 volume aqueous sample with 4 volumes of ethyl acetate/acetone/methanol (70/30/5 v/v). The upper organic layer, obtained after shaking and centrifugation, is collected, dried by solvent evaporation and vacuum, and re-dissolved in HPLC mobile phase (methanol/water (65/35 v/v)). A 20 µL aliquot of reconstituted sample is injected on an HPLC at a flow rate of 1.2 ml/minute through a Macherey-Nagel column (4×250 mm with Nucleosil 10-5 C18) and detected with a UV detector at 230 nm wavelength.

Example 14

PALM Containing Miriplatin Inhibits PC-3 Cell Growth as Well as Cisplatin

Figure 6:
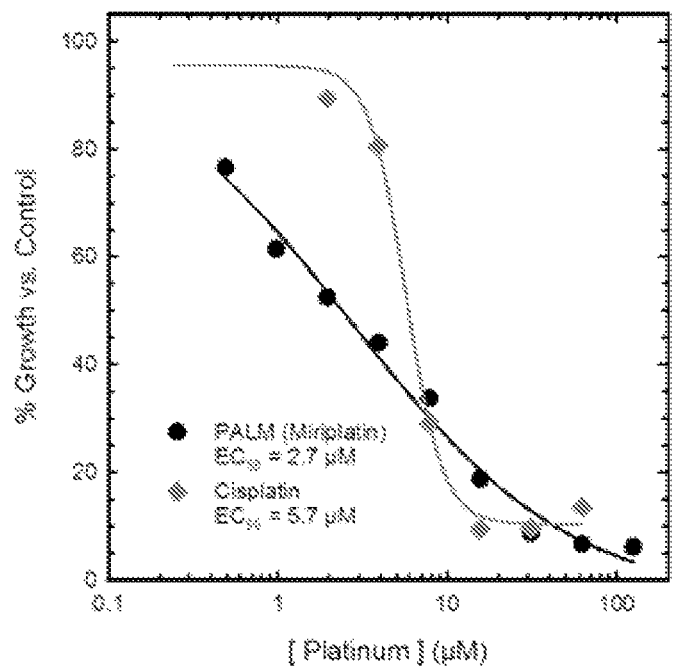
FIG. 6. Inhibition of PC3 prostate cancer cell growth by PALM(MP) compared to inhibition by cisplatin FIG. 7. Effect of SR-BI antibody on inhibition of PC3 prostate cancer cell growth by PALM(MP). The lines indicate fits of the data to the logistic equation.

PC-3cells (American Type Culture Collection, CRL-1435) were seeded in 96-well plates at a density of 5×10³ cells per well (100 µL) and grown till approximately 70% confluence (24 hour) in growth medium composed of F-12K medium supplemented with 10% fetal bovine serum. Next, growth medium was replaced by either 100 µL fresh growth medium (control) or by growth medium supplemented with various concentrations of cisplatin (e.g. 0 µM and 0.1 to 100 µM final concentration in medium) added from 100-fold concentrated stock solutions prepared in 5% dextrose or with equivalent amounts of MP in PALM, as prepared in Example 6. Each condition was tested in triplicate. Plates were incubated for 48 hours. Cell viability was assayed with the thiazolyl blue tetrazolium bromide (MTT) assay by adding 20 µl of 5 mg/ml MTT in Dulbeco's phosphate buffered saline (with calcium and magnesium) and incubating for 3 hours. Next, media were carefully removed and replaced by 200 µL of dimethylsulfoxide (DMSO). The plates were agitated gently for 15 minutes on an orbital shaker. The absorbance of each well was read at 570 nm. The concentration resulting in 50% growth inhibition (IC50) was determined by non-linear regression fit of the data to the logistic equation. The average absorbance of the control wells represented 100% growth (FIG. 6).

Example 15

Figure 7:
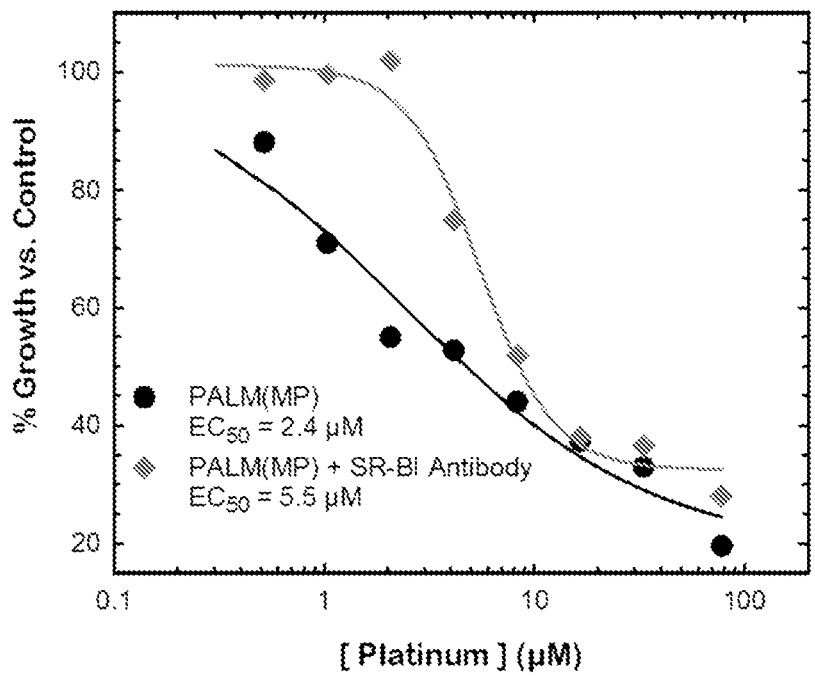

SR-BI Antibody Attenuates PC-3 Cell Growth Inhibition by PALM Containing Miriplatin PC-3cells were grown as in Example 14. Cells to be tested in the presence of SR-BI antibody (Novus Biologics, NB400-113) were preincubated for 1hr in growth medium containing a 1/400 dilution of stock antibody solution. Next, all media were removed and replaced with growth medium containing the indicated amounts of platinum compounds, prepared as in Example 13. The growth media with PALM (MP) for the antibody-treated cells contained antibody at a 1/400 dilution of stock antibody solution. The cells were incubated for 5 hr. Next, all media were removed; the cells were washed one time with medium and then incubated for a further 43 hours in growth medium. Cell survival was determined by MTT assay as in Example 14 (FIG. 7).

Example 16

XT3 in PALM is More Active Than XC in PALM in Blocking SKOV-3 Cell Growth XC

Figure 8:
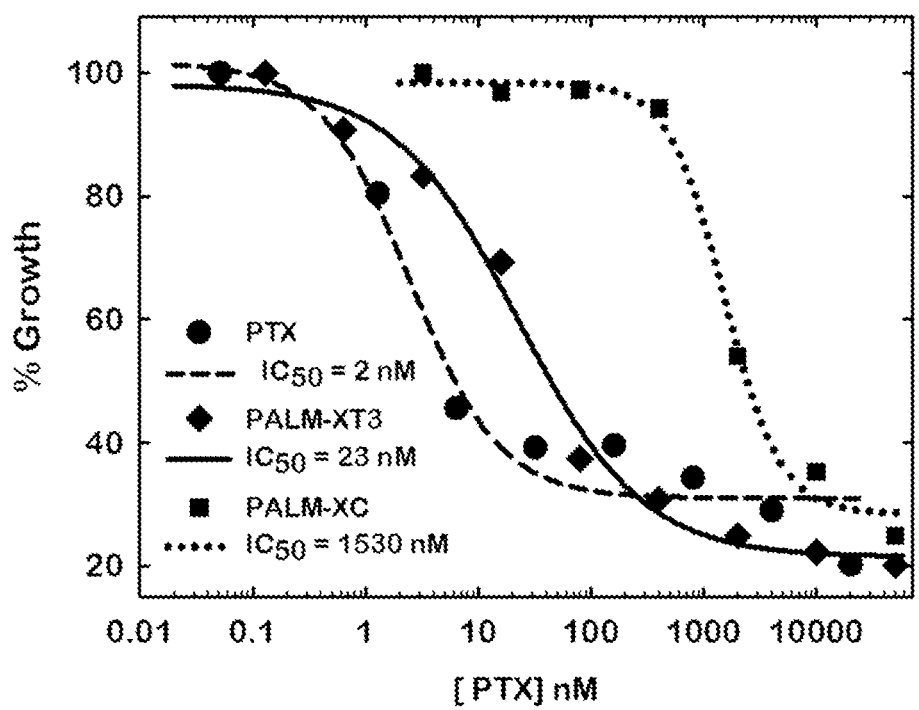
FIG. 8. Inhibition of SKOV3 ovarian cancer cell growth by PALM/(XC) (square, dotted line) or PALM(XT3) (diamond, solid line) compared to inhibition by paclitaxel (circle, dashed line) The lines indicate fits of the data to the logistic equation.

SKOV-3 ovarian cancer cells (American Type Culture Collection, HTB-77) were seeded in 96-well plates at a density of 5×10³ cells per well (100 µL) and grown till approximately 70% confluence (24 hour) in growth medium composed of McCoy's medium supplemented with 10% fetal bovine serum. Next, growth medium was replaced by either 100 μL fresh growth medium (control) or by growth medium supplemented with various concentrations of paclitaxel, PALM(XC) or PALM(XT3). A test solution of 20 μM paclitaxel was prepared by dilution of a 5 mM stock solution of paclitaxel in DMSO into growth medium followed by filter sterilization (0.2 μm filter). An aliquot of the 20 μM solution was diluted 5-fold in growth medium to obtain 4 μM paclitaxel. The 5-fold dilution process was continued with the 4 μM to obtain an 800 nM paclitaxel solution. This process was continued until a concentration of 0.051 nM paclitaxel in growth medium had been obtained. Four 100 μL aliquots of each of the 9 solutions thus obtained were applied to separate wells containing cells. A similar but modified process was used for preparation of PALM(XC) and PALM(XT3) test solutions. The highest concentration tested was 50 μM, which was prepared by dilution of 1 mM preparations (Examples 7, 8) of PALM(XC) and PALM(XT3) in growth medium followed by filter sterilization. The lowest concentration obtained in the process of 5-fold dilution of each newest dilution repeated 8 times was 0.13 nM. Cells were incubated with the test solutions for 72 hours. At the end of this period cell viability was determined by MTT assay, as in Example 14. (FIG. 8).

Example 17

Inhibition of BHK(SR-BI) Cell Growth by PALM(XT3) is SR-BI-Dependent

Figure 10:
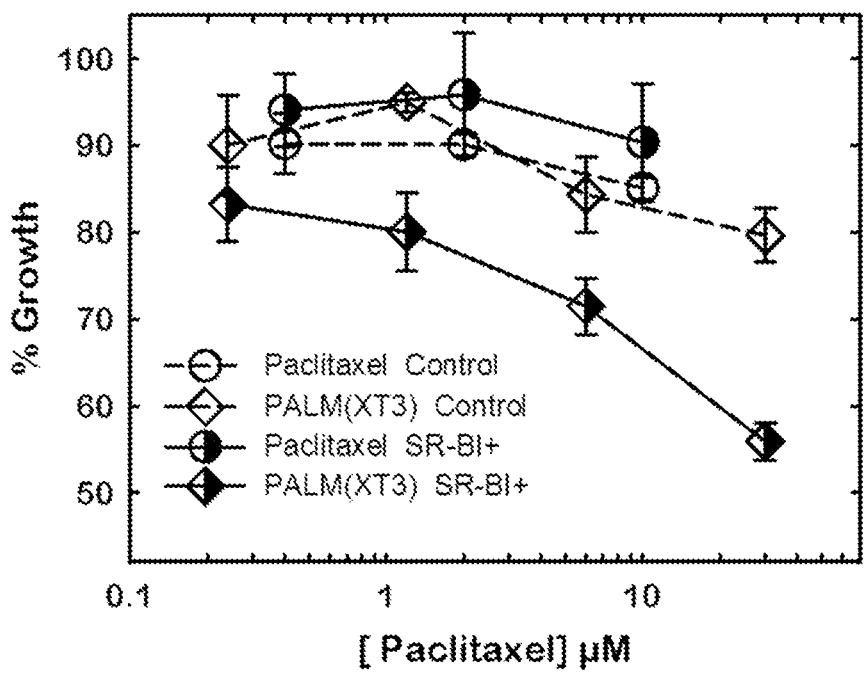
FIG. 10. BHK(SR-BI) cells with a mifepristone inducible, human SR-BI gene, which was either induced (SR-BI+) or un-induced (Control), were incubated with the indicated concentrations of PTX or PALM(XT3) for 12 hours Cells were incubated further in the absence of test agents for an additional 36 hours before detection of % growth by MTT assay.

BHK(SR-BI) cells were plated (3000 cells/well) in 96-well plates with growth medium (Dulbeco's modified Eagle medium containing 10% fetal bovine serum and 200 ug/ml each of zeocin and hygromycin) and incubated 24 hours. Growth medium was replaced with 0.2% bovine serum albumin in Dulbeco's modified Eagle medium containing either 10 nM mifepristone (induced), added from a DMSO stock solution, or the equivalent amount of only DMSO (Control). Cells were incubated for 24 hours. Next, media were replaced with PTX or PALM(XT3) in 0.2% bovine serum albumin in Dulbeco's modified Eagle medium, at the indicated concentrations, and the cells were incubated for 12 hours. Those media were then replaced by normal growth medium and the cells were incubated for 36 hr more. Percent cell growth relative to cells without test agent was determined by MTT assay (FIG. 10).

Example 18

SKOV-3 Ovarian Cell Xenograft Suppression in Nude Mice

The maximum tolerated dose is determined in female mice (Foxn1nu) obtained from commercial suppliers. The efficacy of PALM(XT3) is tested in comparison to Taxol®, which consists of paclitaxel formulated with cremophor EL and ethanol. Each agent is tested at 3 dose levels using 8 mice per level. The Taxol® levels to be tested are 9, 15, 25 mg/kg. Mice are dosed Q2Dx4 intravenously. Separate vehicle control groups are treated with the appropriate volume of saline or cremophor EL/ethanol vehicle. All mice are weighed daily and observed for clinical signs. All mice are held for 14 days after the last dose to detect any delayed toxicity For the efficacy studies, mice are implanted subcutaneously with 30 to 60 mg tumor fragments collected from donor animals. Mice with tumors in excess of 1 g or with ulcerated tumors are euthanized, as are those found in obvious distress or in a moribund condition. Dosing (Q2Dx4) begins when the mean estimated tumor mass for all groups in the experiment is 100-150 mg. There are 10 treatment groups (8 mice per group) comprising a vehicle control group for each of the 2 vehicles, 3 treated groups for Taxol® at 0.6×, 1×, and 1.67× the maximum tolerated dose and 5 groups for PALM(XT3) at 0.3×, 0.6×, 1×, 1.7× and 2.8× the maximum tolerated dose. All mice are observed for clinical signs at least once daily. Body weights and tumor measurements are recorded thrice weekly. Mice continue evaluation for 60 days after the last dose to obtain tumor growth delay data.

Tumor burden (mg) is estimated by the formula for the volume of a prolate ellipsoid assuming unit density as: Tumor burden (mg)=(L×W2)/2, where L and W are the respective orthogonal tumor length and width measurement with calipers (mm). The primary endpoints used to evaluate efficacy are: 1) % T/C which is defined as the median tumor mass of the Treated Group divided by the median tumor mass of the Control Group×100, 2) complete and partial tumor response, 3) tumor growth delay, and 4) the number of tumor-free survivors at the end of the study. The median times to evaluation size for all study groups are analyzed by the log rank test (Kaplan-Meier) to determine if any significant differences exist between groups.

Example 19

δ-Tocotrienyl (N$^4$)-Gemcitabine Carbamate

The hydroxyl groups in gemcitabine are protected by conversion to tert-butoxycarbonyl (BOC) esters with di-tert-butyl dicarbonate following the procedure of Guo and Gallo (J. Org. Chem. 1999, 64, 8319) to yield (1)

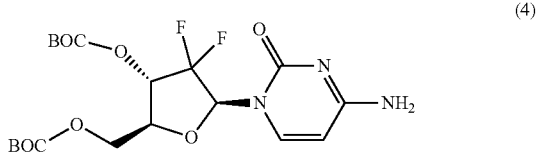 [SMILES: CC(C)(C)OC(=O)OC[C@@H]1O[C@H](n2ccc(N)nc2=O)C(F)(F)[C@H]1OC(=O)OC(C)(C)C]

(4)

Compound 4 is dissolved in anhydrous dichloromethane to a final concentration of 0.2M compound (4). For every mole of compound (4) in solution, 1.2 mole equivalents of compound (2) at 0.5M concentration in methylene chloride and 3 mole equivalents of DMAP are combined at rt. The mixture is stirred at room temperature for 24 h. The resultant product is deprotected with trifluoracetic acid, as referenced. Pure compound is obtained by flash column chromatography using dichloromethane and methanol eluent, beginning with 100% dichloromethane and gradually increasing the concentration to 10% methanol to yield the titled compound (5).

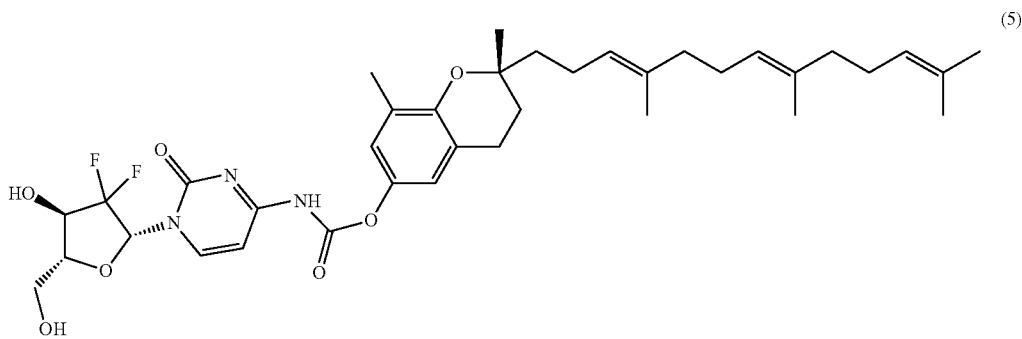 [SMILES: CC(C)=CCC/C(C)=C/CC/C(C)=C/CC[C@]1(C)CCc2cc(OC(=O)Nc3ccn([C@@H]4O[C@H](CO)[C@@H](O)C4(F)F)c(=O)n3)cc(C)c2O1]

(5)

Example 20

Synthesis of (N⁴)-gemcitabine carbamates with the α, ß or γ-tocotrienol isomers is performed similarly to Example 19.

Example 21

Cholesteryl (N⁴)-Gemcitabine Carbamate

The synthesis of cholesteryl (N⁴)-gemcitabine carbamate (6) is performed in the same manner as described in Example 19 with the exception that compound (4) is reacted with cholesterol chloroformate (commercially available) and deprotected as in Example 19 to yield the titled compound (6).

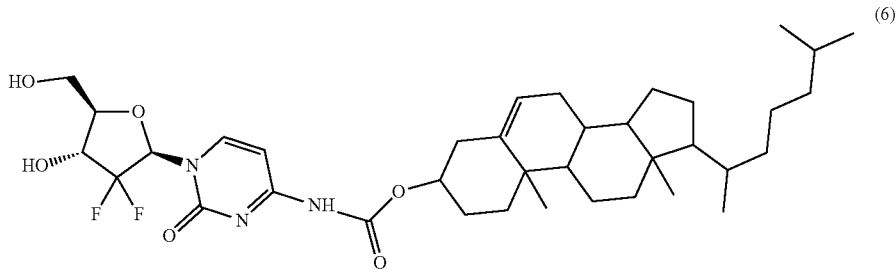 [SMILES: CC(C)CCCC(C)C1CCC2C3CC=C4CC(OC(=O)Nc5ccn([C@@H]6O[C@H](CO)[C@@H](O)C6(F)F)c(=O)n5)CCC4(C)C3CCC12C]

(6)

Example 22

Paclitaxel linked to fatty alcohols via succinic and diglycolic acids

Synthesis of paclitaxel linked to fatty alcohol via a succinate or diglycolate di-ester link is accomplished by reacting fatty alcohol with 4-(dimethylamino)pyridine and succinic anhydride or diglycolic anhydride in anhydrous pyridine with constant stirring for 24 h at room temperature. The reaction is quenched with 0.1 N HCl in dichloromethane. The product is obtained by preparative TLC or flash column chromatography with ethyl acetate in petroleum ether. The alcohol-succinic acid or -diglycolic acid conjugate is combined with 4-(dimethylamino)pyridine and N-(3-dimethylaminopropyl)-N'-ethylcarbodiimide in dry dichloromethane. Paclitaxel is added into the reaction mixture. After 24 h, the reaction is quenched with water and extracted with dichloromethane. The product is obtained by preparative TLC using ethyl acetate/heptanes (50:50) as eluent.

Example 23

Effect of SR-BI Antibody on PALM(XT3) cytotoxicity in SKOV-3 Cells

Figure 11:
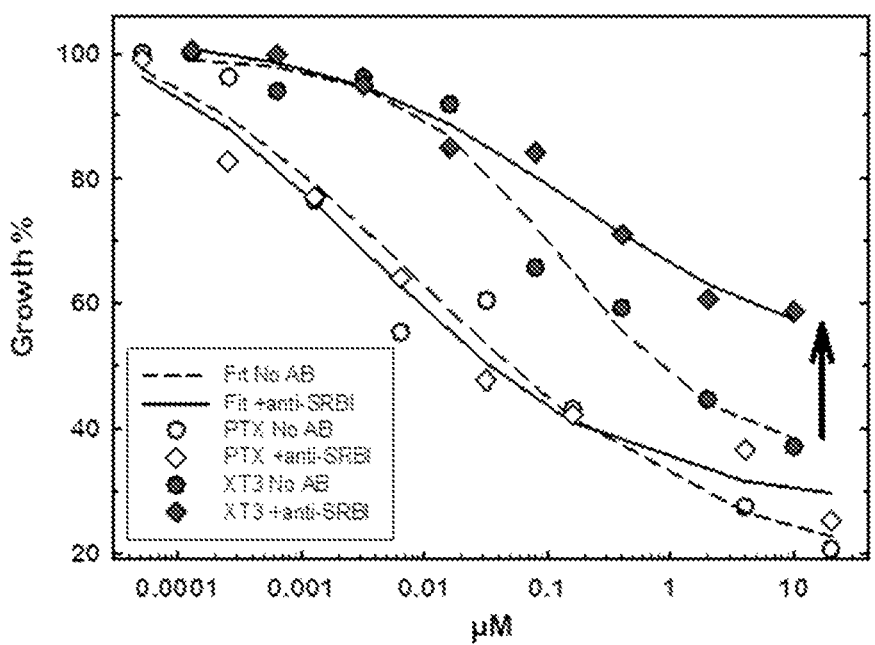
FIG. 11. SR-BI antibody blocks XT3 uptake from PALM (XT3) (arrow).

SKOV-3 were plated and incubated for 24 hour, as in Example 16. Next, growth medium was replaced with serum-free medium containing 0.5% albumin and the indicated concentrations of test agents, with or without anti-SRBI (1/250 dilution) (NB400-113, Novus Biologicals). The cells were incubated 12 hr. Next, the cells were washed with serum-free medium containing 0.5% albumin and grown a further 60 hour in growth medium. Cell growth was detected by MTT assay (FIG. 11).

While a number of embodiments of this disclosure are described, it is apparent that the basic examples may be altered to provide other embodiments that use or encompass methods and processes of this invention. The embodiments and examples are for illustrative purposes and are not to be interpreted as limiting the disclosure, but rather, the appended claims define the scope of this invention.

What is claimed is:

1. A peptide comprising the amino acid sequence: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$, wherein: $X_1$ is the amino acid D; $X_2$ and $X_{20}$ are each the amino acid V; $X_3$, $X_6$, $X_{10}$ and $X_{13}$ are each an amino acid independently selected from the group consisting of L and F; $X_4$, $X_{12}$ and $X_{19}$ are each the amino acid Q; $X_5$ is the amino acid A or Aib; $X_7$, $X_{16}$ and $X_{18}$ are each the amino acid K; $X_8$ and $X_{15}$ are each the amino acid E; $X_9$ and $X_{14}$ are each an amino acid independently selected from the group consisting of A, L, F and Aib; $X_{11}$ is an amino acid selected from the group consisting of A, Aib and N; and $X_{17}$ is an amino acid selected from the group consisting of W, F and L, wherein the peptide is optionally acylated at the N-terminus, amidated at the C-terminus, or both acylated at the N-terminus and amidated at the C-terminus, and the peptide is from 20 to 24 amino acids in length, and wherein the peptide is not DVFQALKELFAQLLEKWKQV (SEQ ID NO: 2); or $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$, wherein: $X_1$ is an amino acid selected from the group consisting of D and E; $X_2$ and $X_{20}$ are each an amino acid independently selected from the group consisting of V, I, and L; $X_3$, $X_6$, $X_{10}$ and $X_{13}$ are each an amino acid independently selected from the group consisting of L, I, V, W, Y, Aib, Amv and F; $X_4$, $X_{12}$ and $X_{19}$ are each an amino acid independently selected from the group consisting of Q and N; $X_5$, $X_{16}$ and $X_{18}$ are each an amino acid independently selected from the group consisting of K, R, H and Orn; $X_7$ is an amino acid selected from the group consisting of A, G, S, V, Aib and Amv; $X_8$ and $X_{15}$ are each an amino acid independently selected from the group consisting of E and D; $X_9$ and $X_{14}$ are each an amino acid independently selected from the group consisting of A, G, S L, F, V, Amv, and Aib; $X_{11}$ is an amino acid selected from the group consisting of A, G, S, Aib, Amv, V and N; and $X_{17}$ is an amino acid selected from the group consisting of W, F, Y, I, V, and L, wherein the peptide is optionally acylated at the N-terminus, amidated at the C-terminus, or both acylated at the N-terminus and amidated at the C-terminus, and the peptide is from 20 to 24 amino acids in length.

2. The peptide of claim 1, comprising an amino acid sequence selected from the group consisting of SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; wherein the peptide is optionally acylated at the N-terminus, amidated at the C-terminus, or both acylated at the N-terminus and amidated at the C-terminus, and the peptide is from 20 to 24 amino acids in length.

3. A peptide amphiphile lipid micelle (PALM) comprising a peptide of claim 1, and a lipid component comprising sphingomyelin and one or more additional phospholipid.

4. The PALM of claim 3, wherein the one or more additional phospholipid is selected from the group consisting of phosphatidylcholine, polyethylene glycol-phosphatidylethanolamine (PEG-PE), phosphatidylethanolamine, phosphatidylglycerol, phosphatidylserine, phosphatidylinositol, cardiolipin, or any combination thereof.

5. A PALM-cargo composition comprising the PALM of claim 3, and at least one cargo molecule.

6. The PALM-cargo composition of claim 5, wherein the at least one cargo molecule is an imaging agent or a drug.

7. The PALM-cargo composition of claim 6, wherein the drug is miriplatin or fenretinide.

8. The PALM-cargo composition of claim 5, wherein the at least one cargo molecule is a conjugate having the formula (I):

A-R-L-X       (formula I), wherein A is an agent having a hydroxyl or an amine group R; L is a linker; and X is an anchor moiety selected from the group consisting of cholesterol, α-tocotrienol, β-tocotrienol, γ-tocotrienol, and δ-tocotrienol.

9. The PALM-cargo composition of claim 8, wherein R is a hydroxyl group and the anchor moiety is covalently bonded to the agent by a carbonate ester bond.

10. The PALM-cargo composition of claim 8, wherein R is an amine group and the anchor moiety is covalently bonded to the agent by a carbamate ester bond.

11. The PALM-cargo composition of claim 8, wherein the agent is a drug.

12. The PALM-cargo composition of claim 11, wherein the drug is an anti-cancer drug.

13. The PALM-cargo composition of claim 12, wherein the anti-cancer drug is a hydroxy camptothecin; daunorubicin; paclitaxel; or docetaxel.

14. The PALM-cargo composition of claim 13, wherein X is β-tocotrienol.

15. The PALM-cargo composition of claim 14, wherein the anti-cancer drug is paclitaxel.

16. The PALM-cargo composition of claim 14, wherein the anti-cancer drug is docetaxel.

17. The PALM-cargo composition of claim 13, wherein X is δ-tocotrienol.

18. The PALM-cargo composition of claim 8, wherein the PALM-cargo composition further comprises an imaging agent.

19. The PALM-cargo composition of claim 8, wherein X is β-tocotrienol.

20. A method for treating a disorder comprising administering to a subject in need thereof, an effective amount of a PALM-cargo composition of claim 11.

21. The method of claim 20, wherein the peptide is selected from the group consisting of SEQ ID NO: 25, SEQ ID NO: 28, SEQ ID NO: 34 and SEQ ID NO: 35.

* * * * *

SEQUENCE LISTING

<160> NUMBER OF SEQ ID NOS: 70

<210> SEQ ID NO 1
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: L or F
<220> FEATURE:
<221> NAME/KEY: MISC_FEATURE
<222> LOCATION: (5)..(5)
<223> OTHER INFORMATION: A or Aib
<220> FEATURE:
<221> NAME/KEY: MISC_FEATURE
<222> LOCATION: (6)..(6)
<223> OTHER INFORMATION: L or F
<220> FEATURE:
<221> NAME/KEY: MISC_FEATURE
<222> LOCATION: (9)..(9)
<223> OTHER INFORMATION: A, L, F, or Aib
<220> FEATURE:
<221> NAME/KEY: MISC_FEATURE
<222> LOCATION: (10)..(10)
<223> OTHER INFORMATION: L or F
<220> FEATURE:
<221> NAME/KEY: MISC_FEATURE
<222> LOCATION: (11)..(11)
<223> OTHER INFORMATION: A, Aib, or N
<220> FEATURE:
<221> NAME/KEY: MISC_FEATURE
<222> LOCATION: (13)..(13)
<223> OTHER INFORMATION: L or F
<220> FEATURE:
<221> NAME/KEY: MISC_FEATURE
<222> LOCATION: (14)..(14)
<223> OTHER INFORMATION: A, L, F, or Aib
<220> FEATURE:
<221> NAME/KEY: MISC_FEATURE
<222> LOCATION: (17)..(17)
<223> OTHER INFORMATION: W, F. or L

<400> SEQUENCE: 1

Asp Val Xaa Gln Xaa Xaa Lys Glu Xaa Xaa Xaa Gln Xaa Xaa Glu Lys
1               5                   10                  15

Xaa Lys Gln Val
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Asp Val Phe Gln Ala Leu Lys Glu Leu Phe Ala Gln Leu Leu Glu Lys
1               5                   10                  15

Trp Lys Gln Val
            20

<210> SEQ ID NO 3
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE

```
<222> LOCATION: (5)..(5)
<223> OTHER INFORMATION: Aib

<400> SEQUENCE: 3

Asp Val Phe Gln Xaa Leu Lys Glu Leu Phe Asn Gln Leu Leu Glu Lys
1               5                   10                  15

Trp Lys Gln Val
            20

<210> SEQ ID NO 4
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Aib

<400> SEQUENCE: 4

Asp Val Phe Gln Xaa Leu Lys Glu Leu Leu Ala Gln Leu Leu Glu Lys
1               5                   10                  15

Phe Lys Gln Val
            20

<210> SEQ ID NO 5
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Aib

<400> SEQUENCE: 5

Asp Val Phe Gln Xaa Leu Lys Glu Leu Leu Asn Gln Leu Leu Glu Lys
1               5                   10                  15

Phe Lys Gln Val
            20

<210> SEQ ID NO 6
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Aib
<220> FEATURE:
<221> NAME/KEY: MISC_FEATURE
<222> LOCATION: (14)..(14)
<223> OTHER INFORMATION: Aib

<400> SEQUENCE: 6

Asp Val Phe Gln Xaa Leu Lys Glu Leu Leu Asn Gln Leu Xaa Glu Lys
1               5                   10                  15

Phe Lys Gln Val
            20

<210> SEQ ID NO 7
<211> LENGTH: 20
<212> TYPE: PRT
```

<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Aib
<220> FEATURE:
<221> NAME/KEY: MISC_FEATURE
<222> LOCATION: (14)..(14)
<223> OTHER INFORMATION: Aib

<400> SEQUENCE: 7

Asp Val Phe Gln Xaa Leu Lys Glu Leu Leu Asn Gln Leu Xaa Glu Lys
1               5                   10                  15

Trp Lys Gln Val
            20

<210> SEQ ID NO 8
<211> LENGTH: 20
<212> TYPE: PRT
<213> ORGANISM: Artificial Sequence
<220> FEATURE:
<223> OTHER INFORMATION: synthetic peptide

<400> SEQUENCE: 8

Asp Val Phe Gln Ala Leu Lys Glu Leu Leu Ala Gln Leu Leu Glu Lys
1               5                   10                  15

Phe Lys Gln Val
            20

<210> SEQ ID NO 9
<211> LENGTH: 20
<212> TYPE: PRT
<213> ORGANISM: Artificial Sequence
<220> FEATURE:
<223> OTHER INFORMATION: synthetic peptide

<400> SEQUENCE: 9

Asp Val Phe Gln Ala Leu Lys Glu Leu Leu Asn Gln Leu Leu Glu Lys
1               5                   10                  15

Phe Lys Gln Val
            20

<210> SEQ ID NO 10
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Aib

<400> SEQUENCE: 10

Asp Val Phe Gln Xaa Leu Lys Glu Leu Phe Ala Gln Leu Leu Glu Lys
1               5                   10                  15

Trp Lys Gln Val
            20

<210> SEQ ID NO 11
<211> LENGTH: 20
<212> TYPE: PRT
<213> ORGANISM: Artificial Sequence
<220> FEATURE:
<223> OTHER INFORMATION: synthetic peptide

```
<220> FEATURE:
<221> NAME/KEY: MISC_FEATURE
<222> LOCATION: (5)..(5)
<223> OTHER INFORMATION: Aib

<400> SEQUENCE: 11

Asp Val Phe Gln Xaa Leu Lys Glu Leu Phe Asn Gln Leu Leu Glu Lys
1               5                   10                  15

Trp Lys Gln Val
            20

<210> SEQ ID NO 12
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Aib

<400> SEQUENCE: 12

Asp Val Phe Gln Xaa Leu Lys Glu Leu Phe Asn Gln Leu Leu Glu Lys
1               5                   10                  15

Phe Lys Gln Val
            20

<210> SEQ ID NO 13
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: Aib

<400> SEQUENCE: 13

Asp Val Phe Gln Ala Leu Lys Glu Leu Phe Ala Gln Leu Xaa Glu Lys
1               5                   10                  15

Trp Lys Gln Val
            20

<210> SEQ ID NO 14
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: Aib

<400> SEQUENCE: 14

Asp Val Phe Gln Ala Leu Lys Glu Leu Phe Asn Gln Leu Xaa Glu Lys
1               5                   10                  15

Trp Lys Gln Val
            20

<210> SEQ ID NO 15
<211> LENGTH: 20
<212> TYPE: PRT
<213> ORGANISM: Artificial Sequence
<220> FEATURE:
```

<223> OTHER INFORMATION: synthetic peptide
<220> FEATURE:
<221> NAME/KEY: MISC_FEATURE
<222> LOCATION: (14)..(14)
<223> OTHER INFORMATION: Aib

<400> SEQUENCE: 15

Asp Val Phe Gln Ala Leu Lys Glu Leu Phe Asn Gln Leu Xaa Glu Lys
1               5                   10                  15

Phe Lys Gln Val
            20

<210> SEQ ID NO 16
<211> LENGTH: 20
<212> TYPE: PRT
<213> ORGANISM: Artificial Sequence
<220> FEATURE:
<223> OTHER INFORMATION: synthetic peptide

<400> SEQUENCE: 16

Asp Val Phe Gln Ala Phe Lys Glu Ala Phe Ala Gln Leu Phe Glu Lys
1               5                   10                  15

Trp Lys Gln Val
            20

<210> SEQ ID NO 17
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: Aib

<400> SEQUENCE: 17

Asp Val Phe Gln Ala Phe Lys Glu Xaa Phe Ala Gln Leu Phe Glu Lys
1               5                   10                  15

Trp Lys Gln Val
            20

<210> SEQ ID NO 18
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (5)..(5)
<223> OTHER INFORMATION: Aib
<220> FEATURE:
<221> NAME/KEY: MISC_FEATURE
<222> LOCATION: (9)..(9)
<223> OTHER INFORMATION: Aib

<400> SEQUENCE: 18

Asp Val Phe Gln Xaa Phe Lys Glu Xaa Phe Ala Gln Leu Phe Glu Lys
1               5                   10                  15

Trp Lys Gln Val
            20

<210> SEQ ID NO 19
<211> LENGTH: 20
<212> TYPE: PRT
<213> ORGANISM: Artificial Sequence

```
<220> FEATURE:
<223> OTHER INFORMATION: synthetic peptide
<220> FEATURE:
<221> NAME/KEY: MISC_FEATURE
<222> LOCATION: (11)..(11)
<223> OTHER INFORMATION: Aib

<400> SEQUENCE: 19

Asp Val Phe Gln Ala Phe Lys Glu Ala Phe Xaa Gln Leu Phe Glu Lys
1               5                   10                  15

Trp Lys Gln Val
            20

<210> SEQ ID NO 20
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: Aib
<220> FEATURE:
<221> NAME/KEY: MISC_FEATURE
<222> LOCATION: (11)..(11)
<223> OTHER INFORMATION: Aib

<400> SEQUENCE: 20

Asp Val Phe Gln Ala Phe Lys Glu Xaa Phe Xaa Gln Leu Phe Glu Lys
1               5                   10                  15

Trp Lys Gln Val
            20

<210> SEQ ID NO 21
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Aib
<220> FEATURE:
<221> NAME/KEY: MISC_FEATURE
<222> LOCATION: (9)..(9)
<223> OTHER INFORMATION: Aib
<220> FEATURE:
<221> NAME/KEY: MISC_FEATURE
<222> LOCATION: (11)..(11)
<223> OTHER INFORMATION: Aib

<400> SEQUENCE: 21

Asp Val Phe Gln Xaa Phe Lys Glu Xaa Phe Xaa Gln Leu Phe Glu Lys
1               5                   10                  15

Trp Lys Gln Val
            20

<210> SEQ ID NO 22
<211> LENGTH: 20
<212> TYPE: PRT
<213> ORGANISM: Artificial Sequence
<220> FEATURE:
<223> OTHER INFORMATION: synthetic peptide

<400> SEQUENCE: 22

Asp Val Phe Gln Ala Leu Lys Glu Leu Phe Asn Gln Leu Leu Glu Lys
1               5                   10                  15
```

Trp Lys Gln Val
            20

<210> SEQ ID NO 23
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: Aib

<400> SEQUENCE: 23

Asp Val Phe Gln Xaa Leu Lys Glu Leu Leu Asn Gln Leu Leu Glu Lys
1               5                   10                  15

Leu Lys Gln Val
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D or E
<220> FEATURE:
<221> NAME/KEY: MISC_FEATURE
<222> LOCATION: (2)..(2)
<223> OTHER INFORMATION: V, I, or L
<220> FEATURE:
<221> NAME/KEY: MISC_FEATURE
<222> LOCATION: (3)..(3)
<223> OTHER INFORMATION: L, I, V, W, Y, Aib, Amv, or F
<220> FEATURE:
<221> NAME/KEY: MISC_FEATURE
<222> LOCATION: (4)..(4)
<223> OTHER INFORMATION: Q or N
<220> FEATURE:
<221> NAME/KEY: MISC_FEATURE
<222> LOCATION: (5)..(5)
<223> OTHER INFORMATION: K, R, H, or Orn
<220> FEATURE:
<221> NAME/KEY: MISC_FEATURE
<222> LOCATION: (6)..(6)
<223> OTHER INFORMATION: L, I, V, W, Y, Aib, Amv, or F
<220> FEATURE:
<221> NAME/KEY: MISC_FEATURE
<222> LOCATION: (7)..(7)
<223> OTHER INFORMATION: A, G, S, V, Aib, or Amv
<220> FEATURE:
<221> NAME/KEY: MISC_FEATURE
<222> LOCATION: (8)..(8)
<223> OTHER INFORMATION: E or D
<220> FEATURE:
<221> NAME/KEY: MISC_FEATURE
<222> LOCATION: (9)..(9)
<223> OTHER INFORMATION: A, G, S L, F, V, Amv, or Aib
<220> FEATURE:
<221> NAME/KEY: MISC_FEATURE
<222> LOCATION: (10)..(10)
<223> OTHER INFORMATION: L, I, V, W, Y, Aib, Amv, or F
<220> FEATURE:
<221> NAME/KEY: MISC_FEATURE
<222> LOCATION: (11)..(11)
<223> OTHER INFORMATION: A, G, S, Aib, Amv, V, or N
<220> FEATURE:
<221> NAME/KEY: MISC_FEATURE
<222> LOCATION: (12)..(12)
<223> OTHER INFORMATION: Q or N

```
<220> FEATURE:
<221> NAME/KEY: MISC_FEATURE
<222> LOCATION: (13)..(13)
<223> OTHER INFORMATION: L, I, V, W, Y, Aib, Amv, or F
<220> FEATURE:
<221> NAME/KEY: MISC_FEATURE
<222> LOCATION: (14)..(14)
<223> OTHER INFORMATION: A, G, S L, F, V, Amv, or Aib
<220> FEATURE:
<221> NAME/KEY: MISC_FEATURE
<222> LOCATION: (15)..(15)
<223> OTHER INFORMATION: E or D
<220> FEATURE:
<221> NAME/KEY: MISC_FEATURE
<222> LOCATION: (16)..(16)
<223> OTHER INFORMATION: K, R, H, or Orn
<220> FEATURE:
<221> NAME/KEY: MISC_FEATURE
<222> LOCATION: (17)..(17)
<223> OTHER INFORMATION: W, F, Y, I, V, or L
<220> FEATURE:
<221> NAME/KEY: MISC_FEATURE
<222> LOCATION: (18)..(18)
<223> OTHER INFORMATION: K, R, H, or Orn
<220> FEATURE:
<221> NAME/KEY: MISC_FEATURE
<222> LOCATION: (19)..(19)
<223> OTHER INFORMATION: Q or N
<220> FEATURE:
<221> NAME/KEY: MISC_FEATURE
<222> LOCATION: (20)..(20)
<223> OTHER INFORMATION: V, I, or L

<400> SEQUENCE: 24

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 25
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Aib

<400> SEQUENCE: 25

Asp Val Phe Gln Lys Leu Xaa Glu Leu Phe Asn Gln Leu Leu Glu Lys
1               5                   10                  15

Trp Lys Gln Val
            20

<210> SEQ ID NO 26
<211> LENGTH: 20
<212> TYPE: PRT
<213> ORGANISM: Artificial Sequence
<220> FEATURE:
<223> OTHER INFORMATION: synthetic peptide

<400> SEQUENCE: 26

Asp Val Phe Gln Lys Leu Val Glu Leu Phe Asn Gln Leu Leu Glu Lys
1               5                   10                  15

Trp Lys Gln Val
            20

<210> SEQ ID NO 27
```

```
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: Aib

<400> SEQUENCE: 27

Asp Val Xaa Gln Lys Leu Phe Glu Leu Phe Asn Gln Leu Leu Glu Lys
1               5                   10                  15

Trp Lys Gln Val
            20

<210> SEQ ID NO 28
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Aib

<400> SEQUENCE: 28

Asp Val Phe Gln Lys Leu Xaa Glu Leu Phe Asn Gln Leu Leu Glu Lys
1               5                   10                  15

Phe Lys Gln Val
            20

<210> SEQ ID NO 29
<211> LENGTH: 20
<212> TYPE: PRT
<213> ORGANISM: Artificial Sequence
<220> FEATURE:
<223> OTHER INFORMATION: synthetic peptide

<400> SEQUENCE: 29

Asp Val Phe Gln Lys Leu Val Glu Leu Phe Asn Gln Leu Leu Glu Lys
1               5                   10                  15

Phe Lys Gln Val
            20

<210> SEQ ID NO 30
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: Aib

<400> SEQUENCE: 30

Asp Val Xaa Gln Lys Leu Phe Glu Leu Phe Asn Gln Leu Leu Glu Lys
1               5                   10                  15

Phe Lys Gln Val
            20

<210> SEQ ID NO 31
<211> LENGTH: 20
<212> TYPE: PRT
<213> ORGANISM: Artificial Sequence
```

```
<220> FEATURE:
<223> OTHER INFORMATION: synthetic peptide
<220> FEATURE:
<221> NAME/KEY: misc_feature
<222> LOCATION: (7)..(7)
<223> OTHER INFORMATION: Aib

<400> SEQUENCE: 31

Asp Val Leu Gln Lys Phe Xaa Glu Leu Phe Asn Gln Leu Leu Glu Lys
1               5                   10                  15

Trp Lys Gln Val
            20

<210> SEQ ID NO 32
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: Aib

<400> SEQUENCE: 32

Asp Val Xaa Gln Lys Phe Leu Glu Leu Phe Asn Gln Leu Leu Glu Lys
1               5                   10                  15

Trp Lys Gln Val
            20

<210> SEQ ID NO 33
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: Aib

<400> SEQUENCE: 33

Asp Val Phe Gln Lys Leu Leu Glu Xaa Phe Asn Gln Leu Leu Glu Lys
1               5                   10                  15

Trp Lys Gln Val
            20

<210> SEQ ID NO 34
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (13)..(13)
<223> OTHER INFORMATION: Aib

<400> SEQUENCE: 34

Asp Val Phe Gln Lys Leu Xaa Glu Leu Phe Asn Gln Xaa Leu Glu Lys
1               5                   10                  15

Trp Lys Gln Val
            20
```

```
<210> SEQ ID NO 35
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (14)..(14)
<223> OTHER INFORMATION: Aib

<400> SEQUENCE: 35

Asp Val Phe Gln Lys Leu Xaa Glu Leu Phe Asn Gln Leu Xaa Glu Lys
1               5                   10                  15

Trp Lys Gln Val
            20

<210> SEQ ID NO 36
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: W, F, or L
<220> FEATURE:
<221> NAME/KEY: MISC_FEATURE
<222> LOCATION: (7)..(7)
<223> OTHER INFORMATION: A, L, F, or Aib
<220> FEATURE:
<221> NAME/KEY: MISC_FEATURE
<222> LOCATION: (8)..(8)
<223> OTHER INFORMATION: L or F
<220> FEATURE:
<221> NAME/KEY: MISC_FEATURE
<222> LOCATION: (10)..(10)
<223> OTHER INFORMATION: A, Aib, or N
<220> FEATURE:
<221> NAME/KEY: MISC_FEATURE
<222> LOCATION: (11)..(11)
<223> OTHER INFORMATION: L or F
<220> FEATURE:
<221> NAME/KEY: MISC_FEATURE
<222> LOCATION: (12)..(12)
<223> OTHER INFORMATION: A, L, F, or Aib
<220> FEATURE:
<221> NAME/KEY: MISC_FEATURE
<222> LOCATION: (15)..(15)
<223> OTHER INFORMATION: L or F
<220> FEATURE:
<221> NAME/KEY: MISC_FEATURE
<222> LOCATION: (16)..(16)
<223> OTHER INFORMATION: A or Aib
<220> FEATURE:
<221> NAME/KEY: MISC_FEATURE
<222> LOCATION: (18)..(18)
<223> OTHER INFORMATION: L or F

<400> SEQUENCE: 36

Val Gln Lys Xaa Lys Glu Xaa Xaa Gln Xaa Xaa Xaa Glu Lys Xaa Xaa
1               5                   10                  15

Gln Xaa Val Asp
            20

<210> SEQ ID NO 37
<211> LENGTH: 20
```

```
<212> TYPE: PRT
<213> ORGANISM: Artificial Sequence
<220> FEATURE:
<223> OTHER INFORMATION: synthetic peptide

<400> SEQUENCE: 37

Val Gln Lys Trp Lys Glu Leu Leu Gln Ala Phe Leu Glu Lys Leu Ala
1               5                   10                  15

Gln Phe Val Asp
            20

<210> SEQ ID NO 38
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: Aib

<400> SEQUENCE: 38

Val Gln Lys Trp Lys Glu Leu Leu Gln Asn Phe Leu Glu Lys Leu Xaa
1               5                   10                  15

Gln Phe Val Asp
            20

<210> SEQ ID NO 39
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: Aib

<400> SEQUENCE: 39

Val Gln Lys Phe Lys Glu Leu Leu Gln Ala Leu Leu Glu Lys Leu Xaa
1               5                   10                  15

Gln Phe Val Asp
            20

<210> SEQ ID NO 40
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: Aib

<400> SEQUENCE: 40

Val Gln Lys Phe Lys Glu Leu Leu Gln Asn Leu Leu Glu Lys Leu Xaa
1               5                   10                  15

Gln Phe Val Asp
            20

<210> SEQ ID NO 41
<211> LENGTH: 20
<212> TYPE: PRT
<213> ORGANISM: Artificial Sequence
<220> FEATURE:
```

<223> OTHER INFORMATION: synthetic peptide
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (16)..(16)
<223> OTHER INFORMATION: Aib

<400> SEQUENCE: 41

Val Gln Lys Phe Lys Glu Xaa Leu Gln Asn Leu Leu Glu Lys Leu Xaa
1               5                   10                  15

Gln Phe Val Asp
            20

<210> SEQ ID NO 42
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (7)..(7)
<223> OTHER INFORMATION: Aib
<220> FEATURE:
<221> NAME/KEY: MISC_FEATURE
<222> LOCATION: (16)..(16)
<223> OTHER INFORMATION: Aib

<400> SEQUENCE: 42

Val Gln Lys Trp Lys Glu Xaa Leu Gln Asn Leu Leu Glu Lys Leu Xaa
1               5                   10                  15

Gln Phe Val Asp
            20

<210> SEQ ID NO 43
<211> LENGTH: 20
<212> TYPE: PRT
<213> ORGANISM: Artificial Sequence
<220> FEATURE:
<223> OTHER INFORMATION: synthetic peptide

<400> SEQUENCE: 43

Val Gln Lys Phe Lys Glu Leu Leu Gln Ala Leu Leu Glu Lys Leu Ala
1               5                   10                  15

Gln Phe Val Asp
            20

<210> SEQ ID NO 44
<211> LENGTH: 20
<212> TYPE: PRT
<213> ORGANISM: Artificial Sequence
<220> FEATURE:
<223> OTHER INFORMATION: synthetic peptide

<400> SEQUENCE: 44

Val Gln Lys Phe Lys Glu Leu Leu Gln Asn Leu Leu Glu Lys Leu Ala
1               5                   10                  15

Gln Phe Val Asp
            20

<210> SEQ ID NO 45
<211> LENGTH: 20
<212> TYPE: PRT
<213> ORGANISM: Artificial Sequence

```
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: Aib

<400> SEQUENCE: 45

Val Gln Lys Trp Lys Glu Leu Leu Gln Ala Phe Leu Glu Lys Leu Xaa
1               5                   10                  15

Gln Phe Val Asp
            20

<210> SEQ ID NO 46
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: Aib

<400> SEQUENCE: 46

Val Gln Lys Trp Lys Glu Leu Leu Gln Asn Phe Leu Glu Lys Leu Xaa
1               5                   10                  15

Gln Phe Val Asp
            20

<210> SEQ ID NO 47
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: Aib

<400> SEQUENCE: 47

Val Gln Lys Phe Lys Glu Leu Leu Gln Asn Phe Leu Glu Lys Leu Xaa
1               5                   10                  15

Gln Phe Val Asp
            20

<210> SEQ ID NO 48
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Aib

<400> SEQUENCE: 48

Val Gln Lys Trp Lys Glu Xaa Leu Gln Ala Phe Leu Glu Lys Leu Ala
1               5                   10                  15

Gln Phe Val Asp
            20

<210> SEQ ID NO 49
<211> LENGTH: 20
<212> TYPE: PRT
```

<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Aib

<400> SEQUENCE: 49

Val Gln Lys Trp Lys Glu Xaa Leu Gln Asn Phe Leu Glu Lys Leu Ala
1               5                   10                  15

Gln Phe Val Asp
            20

<210> SEQ ID NO 50
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Aib

<400> SEQUENCE: 50

Val Gln Lys Phe Lys Glu Xaa Leu Gln Asn Phe Leu Glu Lys Leu Ala
1               5                   10                  15

Gln Phe Val Asp
            20

<210> SEQ ID NO 51
<211> LENGTH: 20
<212> TYPE: PRT
<213> ORGANISM: Artificial Sequence
<220> FEATURE:
<223> OTHER INFORMATION: synthetic peptide

<400> SEQUENCE: 51

Val Gln Lys Trp Lys Glu Phe Leu Gln Ala Phe Ala Glu Lys Phe Ala
1               5                   10                  15

Gln Phe Val Asp
            20

<210> SEQ ID NO 52
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: Aib

<400> SEQUENCE: 52

Val Gln Lys Trp Lys Glu Phe Leu Gln Ala Phe Xaa Glu Lys Phe Ala
1               5                   10                  15

Gln Phe Val Asp
            20

<210> SEQ ID NO 53
<211> LENGTH: 20
<212> TYPE: PRT
<213> ORGANISM: Artificial Sequence
<220> FEATURE:
<223> OTHER INFORMATION: synthetic peptide -continued

```
<220> FEATURE:
<221> NAME/KEY: MISC_FEATURE
<222> LOCATION: (12)..(12)
<223> OTHER INFORMATION: Aib
<220> FEATURE:
<221> NAME/KEY: MISC_FEATURE
<222> LOCATION: (16)..(16)
<223> OTHER INFORMATION: Aib

<400> SEQUENCE: 53

Val Gln Lys Trp Lys Glu Phe Leu Gln Ala Phe Xaa Glu Lys Phe Xaa
1               5                   10                  15

Gln Phe Val Asp
            20

<210> SEQ ID NO 54
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: Aib

<400> SEQUENCE: 54

Val Gln Lys Trp Lys Glu Phe Leu Gln Xaa Phe Ala Glu Lys Phe Ala
1               5                   10                  15

Gln Phe Val Asp
            20

<210> SEQ ID NO 55
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: Aib
<220> FEATURE:
<221> NAME/KEY: MISC_FEATURE
<222> LOCATION: (12)..(12)
<223> OTHER INFORMATION: Aib

<400> SEQUENCE: 55

Val Gln Lys Trp Lys Glu Phe Leu Gln Xaa Phe Xaa Glu Lys Phe Ala
1               5                   10                  15

Gln Phe Val Asp
            20

<210> SEQ ID NO 56
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: Aib
<220> FEATURE:
<221> NAME/KEY: MISC_FEATURE
<222> LOCATION: (12)..(12)
<223> OTHER INFORMATION: Aib
<220> FEATURE:
<221> NAME/KEY: MISC_FEATURE
<222> LOCATION: (16)..(16)
```

<223> OTHER INFORMATION: Aib

<400> SEQUENCE: 56

Val Gln Lys Trp Lys Glu Phe Leu Gln Xaa Phe Xaa Glu Lys Phe Xaa
1               5                   10                  15

Gln Phe Val Asp
            20

<210> SEQ ID NO 57
<211> LENGTH: 20
<212> TYPE: PRT
<213> ORGANISM: Artificial Sequence
<220> FEATURE:
<223> OTHER INFORMATION: synthetic peptide

<400> SEQUENCE: 57

Val Gln Lys Trp Lys Glu Leu Leu Gln Asn Phe Leu Glu Lys Leu Ala
1               5                   10                  15

Gln Phe Val Asp
            20

<210> SEQ ID NO 58
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: Aib

<400> SEQUENCE: 58

Val Gln Lys Leu Lys Glu Leu Leu Gln Asn Leu Leu Glu Lys Leu Xaa
1               5                   10                  15

Gln Phe Val Asp
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: V, I, or L
<220> FEATURE:
<221> NAME/KEY: MISC_FEATURE
<222> LOCATION: (2)..(2)
<223> OTHER INFORMATION: Q or N
<220> FEATURE:
<221> NAME/KEY: MISC_FEATURE
<222> LOCATION: (3)..(3)
<223> OTHER INFORMATION: K, R, H, or Orn
<220> FEATURE:
<221> NAME/KEY: MISC_FEATURE
<222> LOCATION: (4)..(4)
<223> OTHER INFORMATION: W, F, Y, I, V, or L
<220> FEATURE:
<221> NAME/KEY: MISC_FEATURE
<222> LOCATION: (5)..(5)
<223> OTHER INFORMATION: K, R, H, or Orn
<220> FEATURE:
<221> NAME/KEY: MISC_FEATURE
<222> LOCATION: (6)..(6)
<223> OTHER INFORMATION: E or D
<220> FEATURE:
<221> NAME/KEY: MISC_FEATURE

```
<222> LOCATION: (7)..(7)
<223> OTHER INFORMATION: A, G, S, L, F, V, Amv, or Aib
<220> FEATURE:
<221> NAME/KEY: MISC_FEATURE
<222> LOCATION: (8)..(8)
<223> OTHER INFORMATION: L, I, V, W, Aib, Amv, or F
<220> FEATURE:
<221> NAME/KEY: MISC_FEATURE
<222> LOCATION: (9)..(9)
<223> OTHER INFORMATION: Q or N
<220> FEATURE:
<221> NAME/KEY: MISC_FEATURE
<222> LOCATION: (10)..(10)
<223> OTHER INFORMATION: A, G, S, Aib, Amv, V, or N
<220> FEATURE:
<221> NAME/KEY: MISC_FEATURE
<222> LOCATION: (11)..(11)
<223> OTHER INFORMATION: L, I, V, W, Aib, Amv, or F
<220> FEATURE:
<221> NAME/KEY: MISC_FEATURE
<222> LOCATION: (12)..(12)
<223> OTHER INFORMATION: A, G, S, L, F, V, Amv, or Aib
<220> FEATURE:
<221> NAME/KEY: MISC_FEATURE
<222> LOCATION: (13)..(13)
<223> OTHER INFORMATION: E or D
<220> FEATURE:
<221> NAME/KEY: MISC_FEATURE
<222> LOCATION: (14)..(14)
<223> OTHER INFORMATION: A, G, S, V, Aib, or Amv
<220> FEATURE:
<221> NAME/KEY: MISC_FEATURE
<222> LOCATION: (15)..(15)
<223> OTHER INFORMATION: L, I, V, W, Aib, Amv, or F
<220> FEATURE:
<221> NAME/KEY: MISC_FEATURE
<222> LOCATION: (16)..(16)
<223> OTHER INFORMATION: K, R, H, or Orn
<220> FEATURE:
<221> NAME/KEY: MISC_FEATURE
<222> LOCATION: (17)..(17)
<223> OTHER INFORMATION: Q or N
<220> FEATURE:
<221> NAME/KEY: MISC_FEATURE
<222> LOCATION: (18)..(18)
<223> OTHER INFORMATION: L, I, V, W, Aib, Amv, or F
<220> FEATURE:
<221> NAME/KEY: MISC_FEATURE
<222> LOCATION: (19)..(19)
<223> OTHER INFORMATION: V, I, or L
<220> FEATURE:
<221> NAME/KEY: MISC_FEATURE
<222> LOCATION: (20)..(20)
<223> OTHER INFORMATION: E or D

<400> SEQUENCE: 59

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 60
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: Aib

<400> SEQUENCE: 60

Val Gln Lys Trp Lys Glu Leu Leu Gln Asn Phe Leu Glu Xaa Leu Lys
1               5                   10                  15
```

Gln Phe Val Asp
        20

<210> SEQ ID NO 61
<211> LENGTH: 20
<212> TYPE: PRT
<213> ORGANISM: Artificial Sequence
<220> FEATURE:
<223> OTHER INFORMATION: synthetic peptide

<400> SEQUENCE: 61

Val Gln Lys Trp Lys Glu Leu Leu Gln Asn Phe Leu Glu Val Leu Lys
1               5                   10                  15

Gln Phe Val Asp
        20

<210> SEQ ID NO 62
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (18)..(18)
<223> OTHER INFORMATION: Aib

<400> SEQUENCE: 62

Val Gln Lys Trp Lys Glu Leu Leu Gln Asn Phe Leu Glu Phe Leu Lys
1               5                   10                  15

Gln Xaa Val Asp
        20

<210> SEQ ID NO 63
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: Aib

<400> SEQUENCE: 63

Val Gln Lys Phe Lys Glu Leu Leu Gln Asn Phe Leu Glu Xaa Leu Lys
1               5                   10                  15

Gln Phe Val Asp
        20

<210> SEQ ID NO 64
<211> LENGTH: 20
<212> TYPE: PRT
<213> ORGANISM: Artificial Sequence
<220> FEATURE:
<223> OTHER INFORMATION: synthetic peptide

<400> SEQUENCE: 64

Val Gln Lys Phe Lys Glu Leu Leu Gln Asn Phe Leu Glu Val Leu Lys
1               5                   10                  15

Gln Phe Val Asp
        20

<210> SEQ ID NO 65
<211> LENGTH: 20

```
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (18)..(18)
<223> OTHER INFORMATION: Aib

<400> SEQUENCE: 65

Val Gln Lys Phe Lys Glu Leu Leu Gln Asn Phe Leu Glu Phe Leu Lys
1               5                   10                  15

Gln Xaa Val Asp
            20

<210> SEQ ID NO 66
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (14)..(14)
<223> OTHER INFORMATION: Aib

<400> SEQUENCE: 66

Val Gln Lys Trp Lys Glu Leu Leu Gln Asn Phe Leu Glu Xaa Phe Lys
1               5                   10                  15

Gln Leu Val Asp
            20

<210> SEQ ID NO 67
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (18)..(18)
<223> OTHER INFORMATION: Aib

<400> SEQUENCE: 67

Val Gln Lys Trp Lys Glu Leu Leu Gln Asn Phe Leu Glu Leu Phe Lys
1               5                   10                  15

Gln Xaa Val Asp
            20

<210> SEQ ID NO 68
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: Aib

<400> SEQUENCE: 68

Val Gln Lys Trp Lys Glu Leu Leu Gln Asn Phe Xaa Glu Leu Leu Lys
1               5                   10                  15

Gln Phe Val Asp
            20

<210> SEQ ID NO 69
```

```
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: Aib
<220> FEATURE:
<221> NAME/KEY: MISC_FEATURE
<222> LOCATION: (14)..(14)
<223> OTHER INFORMATION: Aib

<400> SEQUENCE: 69

Val Gln Lys Trp Lys Glu Leu Xaa Gln Asn Phe Leu Glu Xaa Leu Lys
1               5                   10                  15

Gln Phe Val Asp
            20

<210> SEQ ID NO 70
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: Aib
<220> FEATURE:
<221> NAME/KEY: MISC_FEATURE
<222> LOCATION: (14)..(14)
<223> OTHER INFORMATION: Aib

<400> SEQUENCE: 70

Val Gln Lys Trp Lys Glu Xaa Leu Gln Asn Phe Leu Glu Xaa Leu Lys
1               5                   10                  15

Gln Phe Val Asp
            20
```